US008329608B2

(12) United States Patent
Knudsen et al.

(10) Patent No.: US 8,329,608 B2
(45) Date of Patent: *Dec. 11, 2012

(54) METHODS OF PREPARATION OF AN OLEFIN OLIGOMERIZATION CATALYST

(75) Inventors: Ronald D. Knudsen, Bartlesville, OK (US); Bruce E. Kreischer, Humble, TX (US); Ronald G. Abbott, Kingwood, TX (US); Steven D. Bridges, Bartlesville, OK (US); Brooke L. Small, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 838 days.

This patent is subject to a terminal disclaimer.

(21) Appl. No.: 12/057,853

(22) Filed: Mar. 28, 2008

(65) Prior Publication Data

US 2008/0177122 A1 Jul. 24, 2008

Related U.S. Application Data

(63) Continuation of application No. 10/783,429, filed on Feb. 20, 2004, now abandoned.

(51) Int. Cl.
*B01J 21/00* (2006.01)
*B01J 23/00* (2006.01)
*B01J 25/00* (2006.01)
*B01J 29/00* (2006.01)
*B01J 31/00* (2006.01)
*B01J 37/00* (2006.01)
*C08F 4/02* (2006.01)
*C08F 4/60* (2006.01)

(52) U.S. Cl. ......... 502/150; 502/100; 502/102; 502/152

(58) Field of Classification Search ............. 501/150; 502/100, 102, 150, 152
See application file for complete search history.

(56) References Cited

U.S. PATENT DOCUMENTS 3,635,869 A 1/1972 Steele et al.
3,819,746 A 6/1974 Katzakian, Jr. et al.
(Continued)

FOREIGN PATENT DOCUMENTS
AU 650808 6/1994
(Continued)

OTHER PUBLICATIONS

Adams, Harry, et al., "Complexes of ligands providing endogenous bridges. Part 1. The syntheses and crystal structures of barium and lead(II) complexes of macrocyclic schiff bases derived from heterocyclic dicarbonyls and 1,n-diamino-n'-hydroxyalkanes (n,n' = 3,2; 4,2; or 5,3)," XP009070491, 1987, pp. 207-218, J. Chem. Soc. Dalton Trans.

(Continued)

*Primary Examiner* — James McDonough
(74) *Attorney, Agent, or Firm* — Conley Rose, P.C.; Rodney B. Carroll; Lynda Jolly

(57) ABSTRACT

A method of making a catalyst for use in oligomerizing an olefin, comprising a chromium-containing compound, a pyrrole-containing compound, a metal alkyl, a halide-containing compound, and optionally a solvent, the method comprising abating all or a portion of water, acidic protons, or both from a composition comprising the chromium-containing compound, a composition comprising the pyrrole-containing compound, a composition comprising a non-metal halide-containing compound, a composition comprising the solvent, or combinations thereof prior to contact thereof with a composition comprising a metal halide-containing compound.

19 Claims, 8 Drawing Sheets

U.S. PATENT DOCUMENTS

| | | | |
|---|---|---|---|
| 3,873,602 | A | 3/1975 | Katzakian, Jr. et al. |
| 3,932,285 | A | 1/1976 | Ceprini et al. |
| 3,962,182 | A | 6/1976 | Steele et al. |
| 3,968,135 | A | 7/1976 | Steele et al. |
| 3,977,996 | A | 8/1976 | Katzakian, Jr. et al. |
| 3,978,026 | A | 8/1976 | Katzakian, Jr. et al. |
| 4,017,429 | A | 4/1977 | Steele et al. |
| 4,057,565 | A * | 11/1977 | Manzer ............................ 534/15 |
| 4,451,573 | A | 5/1984 | Ikegami et al. |
| 4,668,838 | A | 5/1987 | Briggs |
| 4,777,315 | A | 10/1988 | Levine et al. |
| 4,853,356 | A | 8/1989 | Briggs |
| 4,876,229 | A | 10/1989 | Furtek |
| 4,971,986 | A | 11/1990 | Stanek et al. |
| 5,081,089 | A | 1/1992 | Rekers et al. |
| 5,118,648 | A | 6/1992 | Furtek et al. |
| 5,137,994 | A | 8/1992 | Goode et al. |
| 5,198,401 | A | 3/1993 | Turner et al. |
| 5,198,563 | A | 3/1993 | Reagen et al. |
| 5,288,823 | A | 2/1994 | Reagan et al. |
| 5,331,070 | A | 7/1994 | Pettijohn et al. |
| 5,331,104 | A | 7/1994 | Reagen et al. |
| 5,340,785 | A | 8/1994 | Reagen et al. |
| 5,340,892 | A | 8/1994 | Kuramoto |
| 5,360,879 | A | 11/1994 | Reagen et al. |
| 5,376,612 | A * | 12/1994 | Reagen et al. .................. 502/104 |
| 5,382,738 | A | 1/1995 | Reagen et al. |
| 5,393,719 | A | 2/1995 | Pettijohn et al. |
| 5,399,539 | A | 3/1995 | Reagen et al. |
| 5,438,027 | A | 8/1995 | Reagen et al. |
| 5,451,645 | A | 9/1995 | Reagen et al. |
| 5,470,926 | A | 11/1995 | Reagen et al. |
| 5,491,272 | A | 2/1996 | Tanaka et al. |
| 5,523,507 | A | 6/1996 | Reagen et al. |
| 5,543,375 | A | 8/1996 | Lashier et al. |
| 5,550,305 | A | 8/1996 | Wu |
| 5,557,026 | A | 9/1996 | Tanaka et al. |
| 5,563,312 | A | 10/1996 | Knudsen et al. |
| 5,689,028 | A | 11/1997 | Lashier et al. |
| 5,696,240 | A | 12/1997 | Vallarino et al. |
| 5,714,556 | A | 2/1998 | Johnson et al. |
| 5,731,487 | A | 3/1998 | Tamura et al. |
| 5,744,677 | A | 4/1998 | Wu |
| 5,750,816 | A | 5/1998 | Araki et al. |
| 5,750,817 | A | 5/1998 | Tanaka et al. |
| 5,763,723 | A | 6/1998 | Reagen et al. |
| 5,786,291 | A | 7/1998 | Speca et al. |
| 5,786,431 | A | 7/1998 | Reagen et al. |
| 5,811,618 | A | 9/1998 | Wu |
| 5,814,575 | A | 9/1998 | Reagen et al. |
| 5,830,955 | A | 11/1998 | Takeda et al. |
| 5,856,257 | A | 1/1999 | Freeman et al. |
| 5,856,610 | A | 1/1999 | Tamura et al. |
| 5,856,612 | A | 1/1999 | Araki et al. |
| 5,859,303 | A | 1/1999 | Lashier |
| 5,910,619 | A | 6/1999 | Urata et al. |
| 5,919,996 | A | 7/1999 | Freeman et al. |
| 5,955,555 | A | 9/1999 | Bennett |
| 5,968,866 | A | 10/1999 | Wu |
| 5,986,153 | A | 11/1999 | Kallenbach et al. |
| 6,031,145 | A | 2/2000 | Commereuc et al. |
| 6,063,881 | A | 5/2000 | Bennett |
| 6,103,654 | A | 8/2000 | Commereuc et al. |
| 6,103,658 | A | 8/2000 | Mackenzie et al. |
| 6,103,946 | A | 8/2000 | Brookhart, III et al. |
| 6,127,301 | A | 10/2000 | Iwanaga et al. |
| 6,133,495 | A | 10/2000 | Urata et al. |
| 6,150,482 | A | 11/2000 | Brookhart et al. |
| 6,214,761 | B1 | 4/2001 | Bennett |
| 6,221,986 | B1 | 4/2001 | Commereuc et al. |
| 6,239,237 | B1 | 5/2001 | Xu et al. |
| 6,281,303 | B1 | 8/2001 | Lavoie et al. |
| 6,291,733 | B1 | 9/2001 | Small et al. |
| 6,337,297 | B1 | 1/2002 | Mimura et al. |
| 6,344,594 | B1 | 2/2002 | Sen et al. |
| 6,369,177 | B1 | 4/2002 | Tohi et al. |
| 6,380,451 | B1 * | 4/2002 | Kreischer et al. .............. 585/502 |
| 6,414,098 | B1 | 7/2002 | Engehausen et al. |
| 6,417,305 | B2 | 7/2002 | Bennett |
| 6,417,364 | B1 | 7/2002 | Lenges |
| 6,423,848 | B2 | 7/2002 | Bennett |
| 6,451,939 | B1 | 9/2002 | Britovsek et al. |
| 6,455,648 | B1 | 9/2002 | Freeman et al. |
| 6,458,739 | B1 | 10/2002 | Kimberley et al. |
| 6,458,905 | B1 | 10/2002 | Schmidt et al. |
| 6,461,994 | B1 | 10/2002 | Gibson et al. |
| 6,465,386 | B1 | 10/2002 | Maddox et al. |
| 6,489,497 | B1 | 12/2002 | Brookhart, III et al. |
| 6,521,806 | B1 | 2/2003 | Tamura et al. |
| 6,534,691 | B2 | 3/2003 | Culver et al. |
| 6,545,108 | B1 | 4/2003 | Moody et al. |
| 6,548,672 | B1 | 4/2003 | Gibson et al. |
| 6,555,633 | B1 | 4/2003 | Tanaka et al. |
| 6,555,723 | B2 | 4/2003 | Schiffino |
| 6,562,973 | B1 | 5/2003 | Liu |
| 6,683,187 | B2 | 1/2004 | De Boer et al. |
| 6,689,848 | B2 | 2/2004 | Nagy et al. |
| 6,710,006 | B2 | 3/2004 | De Boer et al. |
| 6,740,715 | B2 | 5/2004 | Brookhart, III et al. |
| 6,777,584 | B2 | 8/2004 | Patil et al. |
| 6,828,269 | B2 | 12/2004 | Commereuc et al. |
| 6,841,693 | B1 | 1/2005 | Watanabe et al. |
| 6,844,290 | B1 | 1/2005 | Maas et al. |
| 6,900,152 | B2 | 5/2005 | Yoshida et al. |
| 6,903,042 | B2 | 6/2005 | Drochon et al. |
| 6,911,505 | B2 | 6/2005 | Small |
| 6,911,506 | B2 | 6/2005 | Small et al. |
| 6,927,313 | B2 | 8/2005 | Bianchini et al. |
| 7,001,964 | B2 | 2/2006 | Small |
| 7,037,988 | B2 | 5/2006 | De Boer et al. |
| 7,045,632 | B2 | 5/2006 | Small |
| 7,049,442 | B2 | 5/2006 | De Boer et al. |
| 7,053,259 | B2 | 5/2006 | Culver et al. |
| 7,129,304 | B1 | 10/2006 | Small et al. |
| 7,176,266 | B2 | 2/2007 | Sato et al. |
| 7,179,871 | B2 | 2/2007 | De Boer et al. |
| 7,223,893 | B2 | 5/2007 | Small et al. |
| 7,238,764 | B2 | 7/2007 | De Boer et al. |
| 7,268,096 | B2 | 9/2007 | Small et al. |
| 7,271,121 | B2 | 9/2007 | Small et al. |
| 7,297,806 | B2 | 11/2007 | Brookhart, III et al. |
| 7,304,159 | B2 | 12/2007 | De Boer et al. |
| 7,442,819 | B2 | 10/2008 | Ionkin et al. |
| 7,456,284 | B2 | 11/2008 | Small |
| 7,589,245 | B2 | 9/2009 | De Boer et al. |
| 2001/0053742 | A1 | 12/2001 | Knudsen et al. |
| 2002/0035029 | A1 | 3/2002 | Yoshida et al. |
| 2003/0130551 | A1 | 7/2003 | Drochon et al. |
| 2004/0116758 | A1 | 6/2004 | De Boer et al. |
| 2004/0122269 | A1 | 6/2004 | Van Zon et al. |
| 2004/0122271 | A1 | 6/2004 | Van Zon et al. |
| 2005/0187098 | A1 | 8/2005 | Knudsen et al. |
| 2005/0187391 | A1 | 8/2005 | Knudsen et al. |
| 2005/0187418 | A1 | 8/2005 | Small et al. |
| 2007/0043181 | A1 | 2/2007 | Knudsen et al. |
| 2007/0112150 | A1 | 5/2007 | Small et al. |
| 2008/0058534 | A1 | 3/2008 | Knudsen et al. |
| 2009/0270567 | A1 | 10/2009 | Small et al. |

FOREIGN PATENT DOCUMENTS

| | | |
|---|---|---|
| CA | 2087578 A1 | 7/1994 |
| CA | 2396614 A1 | 7/2001 |
| CA | 2115639 C | 10/2004 |
| CN | 1256968 | 6/2000 |
| CN | 1294109 | 5/2001 |
| CN | 1306014 A | 8/2001 |
| CN | 1358772 A | 7/2002 |
| CN | 1361093 | 7/2002 |
| CN | 1374281 A | 10/2002 |
| CN | 1850339 A | 10/2006 |
| EP | 0416815 A2 | 3/1991 |
| EP | 0537609 A2 | 4/1993 |
| EP | 0608447 A1 | 8/1994 |
| EP | 0668105 A2 | 8/1995 |
| EP | 1110930 A1 | 6/2001 |
| EP | 1188762 A1 | 3/2002 |
| EP | 1229020 A1 | 8/2002 |

| | | | | | | |
|---|---|---|---|---|---|---|
| EP | 1325924 | A1 | 7/2003 | JP | 11092408 | 4/1999 |
| FR | 2833191 | A1 | 6/2003 | JP | 2000176291 | 6/2000 |
| FR | 2857964 | A1 | 1/2005 | JP | 2000202299 | 7/2000 |
| JP | 6263822 | | 9/1994 | JP | 2000212212 | 8/2000 |
| JP | 7010780 | | 1/1995 | JP | 2001002724 | 1/2001 |
| JP | 7017878 | | 1/1995 | JP | 2001009290 | 1/2001 |
| JP | 7018013 | | 1/1995 | JP | 2001096164 | 4/2001 |
| JP | 7118173 | | 5/1995 | JP | 2001149788 | 6/2001 |
| JP | 7118174 | | 5/1995 | JP | 2001187345 | 7/2001 |
| JP | 7118175 | | 5/1995 | JP | 2002045703 | 2/2002 |
| JP | 7118324 | | 5/1995 | JP | 2002066329 | 3/2002 |
| JP | 7118325 | | 5/1995 | JP | 2002102710 | 4/2002 |
| JP | 7118326 | | 5/1995 | JP | 2002172327 | 6/2002 |
| JP | 7118327 | | 5/1995 | JP | 2002200429 | 7/2002 |
| JP | 7118328 | | 5/1995 | JP | 2002205960 | 7/2002 |
| JP | 7149671 | | 6/1995 | JP | 2002233764 | 8/2002 |
| JP | 7149672 | | 6/1995 | JP | 2002233765 | 8/2002 |
| JP | 7149673 | | 6/1995 | JP | 2003071294 | 3/2003 |
| JP | 7149674 | | 6/1995 | JP | 2003088760 | 3/2003 |
| JP | 7149675 | | 6/1995 | JP | 2004136270 | 5/2004 |
| JP | 7149676 | | 6/1995 | JP | 2004136271 | 5/2004 |
| JP | 7149677 | | 6/1995 | JP | 2004306014 | 11/2004 |
| JP | 7157512 | | 6/1995 | KR | 20030029253 | 4/2003 |
| JP | 7215896 | | 8/1995 | WO | 9415940 A1 | 7/1994 |
| JP | 8059732 | | 3/1996 | WO | 9623010 A2 | 8/1996 |
| JP | 8134131 | | 5/1996 | WO | 9827124 A1 | 6/1998 |
| JP | 8151409 | | 6/1996 | WO | 9919280 A1 | 4/1999 |
| JP | 8183747 | | 7/1996 | WO | 9962963 A1 | 12/1999 |
| JP | 8239330 | | 9/1996 | WO | 9962967 A2 | 12/1999 |
| JP | 8239331 | | 9/1996 | WO | 0020427 A1 | 4/2000 |
| JP | 8239418 | | 9/1996 | WO | 0037175 A1 | 6/2000 |
| JP | 8245429 | | 9/1996 | WO | 0068280 A1 | 11/2000 |
| JP | 8245430 | | 9/1996 | WO | 0069923 A1 | 11/2000 |
| JP | 8245431 | | 9/1996 | WO | 0110875 A1 | 2/2001 |
| JP | 8283330 | | 10/1996 | WO | 0136379 A1 | 5/2001 |
| JP | 8283332 | | 10/1996 | WO | 0136503 A1 | 5/2001 |
| JP | 8301921 | | 11/1996 | WO | 0138270 A1 | 5/2001 |
| JP | 8301922 | | 11/1996 | WO | 0147839 A1 | 7/2001 |
| JP | 8301923 | | 11/1996 | WO | 0148028 A1 | 7/2001 |
| JP | 8301924 | | 11/1996 | WO | 0158874 A1 | 8/2001 |
| JP | 8301925 | | 11/1996 | WO | 0168572 A1 | 9/2001 |
| JP | 8325317 | | 12/1996 | WO | 0168725 A2 | 9/2001 |
| JP | 8325318 | | 12/1996 | WO | 0174830 A1 | 10/2001 |
| JP | 8325319 | | 12/1996 | WO | 0183447 A2 | 11/2001 |
| JP | 8333407 | | 12/1996 | WO | 0200339 A2 | 1/2002 |
| JP | 9012627 | | 1/1997 | WO | 0204119 A1 | 1/2002 |
| JP | 9020692 | | 1/1997 | WO | 0210133 A1 | 2/2002 |
| JP | 9020693 | | 1/1997 | WO | 0228805 A2 | 4/2002 |
| JP | 9040710 | | 2/1997 | WO | 0234701 A1 | 5/2002 |
| JP | 9087318 | | 3/1997 | WO | 02066404 A1 | 8/2002 |
| JP | 9143213 | | 6/1997 | WO | 02066405 A1 | 8/2002 |
| JP | 9176228 | | 7/1997 | WO | 02079276 A2 | 10/2002 |
| JP | 9176229 | | 7/1997 | WO | 02083306 A2 | 10/2002 |
| JP | 9188634 | | 7/1997 | WO | 02083306 A3 | 10/2002 |
| JP | 9194400 | | 7/1997 | WO | 02096919 A1 | 12/2002 |
| JP | 9194524 | | 7/1997 | WO | 03004158 A2 | 1/2003 |
| JP | 9262480 | | 10/1997 | WO | 03011876 A1 | 2/2003 |
| JP | 9268133 | | 10/1997 | WO | 03024902 A1 | 3/2003 |
| JP | 9268134 | | 10/1997 | WO | 03053890 A1 | 7/2003 |
| JP | 9268135 | | 10/1997 | WO | 03053891 A1 | 7/2003 |
| JP | 10007593 | | 1/1998 | WO | 03059511 A1 | 7/2003 |
| JP | 10007594 | | 1/1998 | WO | 2004043887 A2 | 5/2004 |
| JP | 10007595 | | 1/1998 | WO | 2004056477 A1 | 7/2004 |
| JP | 10007681 | | 1/1998 | WO | 2004056478 A1 | 7/2004 |
| JP | 10036431 | | 2/1998 | WO | 2004056479 A1 | 7/2004 |
| JP | 10036432 | | 2/1998 | WO | 2004056480 A1 | 7/2004 |
| JP | 10036433 | | 2/1998 | WO | 2004078799 A1 | 9/2004 |
| JP | 10036435 | | 2/1998 | WO | 2005082816 A1 | 9/2005 |
| JP | 10045634 | | 2/1998 | WO | 2005092821 A1 | 10/2005 |
| JP | 10045638 | | 2/1998 | WO | 2005111099 A1 | 11/2005 |
| JP | 10045833 | | 2/1998 | WO | 2006008438 A1 | 1/2006 |
| JP | 10060043 | | 3/1998 | WO | 2006016101 A1 | 2/2006 |
| JP | 10087517 | | 4/1998 | WO | 2007021955 A2 | 2/2007 |
| JP | 10087518 | | 4/1998 | WO | 2007024504 A1 | 3/2007 |
| JP | 10101587 | | 4/1998 | WO | 2007059015 A1 | 5/2007 |
| JP | 10218799 | | 8/1998 | WO | 2007080081 A2 | 7/2007 |
| JP | 11060511 | | 3/1999 | WO | 2008038173 A2 | 4/2008 |
| JP | 11060626 | | 3/1999 | WO | 2009085411 A1 | 11/2009 |
| JP | 11092407 | | 4/1999 | | | |

OTHER PUBLICATIONS

Allen, Geoffrey, Editor, "Comprehensive polymer science, vol. 4," 1989, pp. 1-108, 409-412, 533-584 plus 1 cover page, 2 publishing pages, and 2 contents pages, Pergamon Press, England.

Boor, Jr., John, "Ziegler-natta catalysts and polymerizations,"1979, 1 cover page and 1 publishing page, Academic Press, Inc., New York.

Brintzinger, Hans H., et al., "Stereospecific olefin polymerization with chiral metallocene catalysts," Angew. Chem. Int. Ed. Engl., 1995, pp. 1143-1170, VCH Verlagsgesellschaft mbH, Weinheim.

Britovsek, George J. P., et al., "Oligomerisation of ethylene by bis(imino)pyridyliron and -cobalt complexes," Chem. Eur. J., 2000, pp. 2221-2231, vol. 6, No. 12, Wiley-VCH Verlag GmbH, Weinheim.

Foreign communication from a related counterpart application—International Search Report, PCT/US2004/004472, Jul. 16, 2004, 3 pages.

Foreign communication from a related counterpart application—International Search Report and Written Opinion, PCT/US2005/005437, Jul. 4, 2005, 13 pages.

Foreign communication from a related counterpart application—International Search Report and Written Opinion, PCT/US2005/042175, Aug. 17, 2006, 9 pages.

Foreign communication from a counterpart application—International Search Report and Written Opinon, PCT/US2008/083026, Mar. 19, 2009, 9 pages.

Kumar, R. N., et al., "Mononuclear and binuclear complexes of Fe(II) and Cu(II) with 2,6-diacetyl pyridine monoxime and phenylene diamine," Jul.-Sep. 1999, pp. 964-969 plus 1 cover page, vol. 11, No. 3, Asian Journal of Chemistry.

Li, Yuesheng, et al., "Preparation of iron—or cobalt-based polynuclear pyridine-containing diimine catalysts for olefin polymerization," XP-002284349, Jun. 14, 2004, 1 page, CAPLUS.

Mark, Herman F., Editor, "Encyclopedia of polymer science and engineering," vol. 6, 1986, pp. 383-522 plus 1 cover page, 2 publishing pages, and 1 contents page, John Wiley & Sons, Inc., USA.

Nelson, S. Martin, et al., "Metal-ion controlled reactions of 2,6-diacetylpyridine with 1,2-diaminoethane and 2,6-diformylpyridine with o-phenylenediamine and the crystal and molecular structure of a pentagonal pyramidal cadmium (II) complex containing unidentate o-phenylenediamine," 1982, pp. 407-415, J.C.S. Dalton.

Small, Brooke L., et al., "Highly active iron and cobalt catalysts for the polymerization of ethylene," Journal of the American Chemical Society, 1998, pp. 4049-4050 plus 1 cover page, vol. 120, No. 16, American Chemical Society.

Small, Brooke L., et al., "Iron-based catalysts with exceptionally high activities and selectivities for oligomerization of ethylene to linear a-olefins," Journal of the American Chemical Society, 1998, pp. 7143-7144 plus 1 cover page, American Chemical Society.

Small, Brooke L., et al., "Polymerization of propylene by a new generation of iron catalysts: mechanisms of chain initiation, propagation, and termination," Macromolecules, 1999, pp. 2120-2130, vol. 32, No. 7, American Chemical Society.

Esteruelas, Miguel A., et al., "Preparation, Structure and Ethylene Polymerization Behavior of Bis (imino) pyridyl Chromium(III) Complexes," Organometallics—American Chemical Society, Jan. 1, 2003, pp. 395-406, vol. 22.

Small, Brooke L, et al., "Iron Catalysts for the Head-to-Head Dimerization of a-Olefins and Mechanistic Implications for the Production of Linear a-Olefins," Organometallics—American Chemical Society, Nov. 22, 2001, pp. 5738-5744, vol. 20.

Foreign communication from a related counterpart application—International Preliminary Report on Patentability, PCT/US2005/005416, Aug. 22, 2006, 6 pages.

Foreign communication from a related counterpart application—International Preliminary Report on Patentability, PCT/US2006/031303, Feb. 20, 2008, 7 pages.

Office Action dated Jun. 12, 2009, (53 pages) U.S. Appl. No. 11/928,756, filed Oct. 30, 2007.

Patent application entitled "Methods of Preparation of an Olefin Oligomerization Catalyst," by Ronald Knudsen, filed Aug. 17, 2009 as U.S. Appl. No. 12/534,536.

Foreign communication from a counterpart application—European Search Report, EP10183724.3, Jan. 27, 2012, 6 pages.

Foreign communication from a counterpart application—European Search Report, EP10183728.4, Jan. 26, 2012, 7 pages.

Foreign communication from a counterpart application—European Search Report, EP10183732.6, Jan. 27, 2012, 5 pages.

Notice of Allowance dated Nov. 12, 2010, (21 pages), U.S. Appl. No. 11/963,252, filed Dec. 21, 2007.

Foreign communication from a counterpart application CA2745808, Examination Report, Oct. 3, 2011, 2 pages.

Foreign communication from a counterpart application CN200580012496.3, Examination Report, Sep. 14, 2011, 4 pages.

Office Action (Final) dated Feb. 4, 2010, (23 pages), U.S. Appl. No. 11/928,756, filed Oct. 30, 2007.

Office Action dated Jun. 9, 2010, (72 pages), U.S. Appl. No. 11/963,252, filed Dec. 21, 2007.

Office Action dated Jun. 21, 2010 (15 pages), U.S. Appl. No. 12/534,536, filed Aug. 3, 2009.

Foreign communication from a counterpart application CN200580012496.3, Examination Report, May 2, 2012, 5 pages.

Advisory Action dated Aug. 9, 2006 (3 pages), U.S. Appl. No. 10/783,429, filed Feb. 20, 2004.

Advisory Action dated Mar. 29, 2007 (3 pages), U.S. Appl. No. 10/783,429, filed Feb. 20, 2004.

Foreign communication from a counterpart application No. CA 2,556,879 filed Feb. 18, 2005—Filing of Prior Art under Section 34.1 of the Patent Act Protest under Section 10 of the Patent Rules, Jan. 11, 2008, 11 pages.

Foreign communication from a counterpart application—Written Opinion, SG 200605612-1, Aug. 28, 2007, 5 pages.

Notice of Allowance and Fee(s) Due dated Apr. 4, 2008 (14 pages), U.S. Appl. No. 10/783,737, filed on Feb. 20, 2004.

Agapie, Theodor, et al., "Mechanistic studies of the ethylene trimerization reaction with chromium—diphosphine catalysts: experimental evidence for a mechanism involving metallacyclic intermediates," J. Am. Chem. Soc. 2004, pp. 1304-1305, vol. 126, No. 5, American Chemical Society.

Agapie, Theodor, et al., "Structural and mechanistic studies of a chromium—diphosphine system for catalytic trimerization of ethylene," INOR 494, Mar. 28-Apr. 1, 2004, 1 page, The 227th ACS National Meeting, Anaheim, California.

"Aldrich," Catalog Handbook of Fine Chemicals, Aldrich Chemical Company, 1990-1991, Cover page, Information Sheet, and pp. 1274-1275.

Alobaidi, Fahad, et al., "Direct synthesis of linear low-density polyethylene of ethylene/1-hexene from ethylene with a tandem catalytic system in a single reactor," Journal of Polymer Science, 2004, pp. 4327-4336, vol. 42, Wiley Periodicals, Inc.

Andes, Cecily, et al., "New tantalum-based catalyst system for the selective trimerization of ethene to 1-hexene," J. Am. Chem. Soc., 2001, pp. 7423-7424, vol. 123, No. 30, American Chemical Society.

Blok, Arno N. J., et al., "Mechanism of ethene trimerization at an ansa-(arene) (cyclopentadienyl) titanium fragment," Organometallics, 2003, pp. 2564-2570, vol. 22, No. 13, American Chemical Society.

Bollmann, Annette, et al., "Ethylene tetramerization: a new route to produce 1-octene in exceptionally high selectivities," J. Am. Chem. Soc., 2004, pp. 14712-14713, vol. 126, No. 45, American Chemical Society.

Briggs, John R., "The selective trimerization of ethylene to hex-1-ene," 1989, pp. 674-675, J. Chem. Soc., Chem. Commun.

Carter, Anthea, et al., "High activity ethylene trimerisation catalysts based on diphosphine ligands," Chem. Commun., 2002, pp. 858-859, The Royal Society of Chemistry.

Chen, Jwu-Ting, et al., "Dimerization and oligomerization of ethylene catalyzed by a palladium(II) complex with imine-phosphine ligand," National Taiwan University, Taipei, Taiwan, 2000, pp. 279-281, vol. 47, No. 1, Journal of the Chinese Chemical Society.

Dai, Changhua, "Commercialization of 1-hexene by ethylene trimerization in China," Nov. 2002, pp. 25-29, vol. 10, No. 11, Petroleum & Petrochemical Today.

De Bruin, Theodorus J. M., et al., "Hemilabile ligand induced selectivity: a DFT study on ethylene trimerization catalyzed by titanium complexes," Organometallics, 2003, pp. 3404-3413, vol. 22, No. 17, American Chemical Society.

DeWet-Roos, Deon, et al., "Homogeneous tandem catalysis of bis(2-decylthioethyl)amine—chromium trimerization catalyst in combination with metallocene catalysts," Macromolecules, 2004, pp. 9314-9320, vol. 37, No. 25, American Chemical Society.

Deckers, Patrick J. W., et al., "Catalytic trimerization of ethene with highly active cyclopentadienyl—arene titanium catalysts," Organometallics, 2002, pp. 5122-5135, vol. 21, No. 23, American Chemical Society.

Deckers, Patrick J. W., et al., "Switching a catalyst system from ethene polymerization to ethene trimerization with a hemilabile ancillary ligand," Angew. Chem. Int. Ed., 2001, pp. 2516-2519, vol. 40, No. 13, Wiley-VCH Verlag GmbH, D-69451 Weinheim.

Dixon, John T., et al., "Advances in selective ethylene trimerisation—a critical overview," 2004, pp. 3641-3668, vol. 689, Elsevier B.V.

Emrich, Rainer, "The role of metallacycles in the chromium-catalyzed trimerization of ethylene," Organometallics, Apr. 15, 1997, pp. 1511-1513, vol. 16, No. 8, American Chemical Society.

Fang, Yiqun, et al., "A new chromium-based catalyst coated with paraffin for ethylene oligomerization and the effect of chromium state on oligomerization selectivity," Applied Catalysis A: General, 2002, pp. 33-38, vol. 235, Elsevier Science B.V.

Foreign communication from a related counterpart application—International Search Report and Written Opinion, PCT/US2005/005416, Jun. 1, 2005, 10 pages.

Foreign communication from a related counterpart application—International Search Report and Written Opinion, PCT/US2006/031303, Dec. 19, 2006, 13 pages.

Foreign communication from a related counterpart application—EP Examination Report, 05723396.7-2109, Oct. 10, 2007, 4 pages.

Freemen, J. W., et al., "Selective production of 1-hexene from ethylene," Florida Catalysis Conference, Apr. 19-23, 1999, 30 pages.

Hessen, Bart, "Monocyclopentadienyl titanium catalysts: ethene polymerisation versus ethene trimerisation," Journal of Molecular Catalysis A: Chemical, 2004, pp. 129-135, vol. 213, Elsevier B.V.

Huang, Jiling, et al., "Ethylene trimerization with a half-sandwich titanium complex bearing a pendant thienyl group," Chem Commun, 2003, pp. 2816-2817, The Royal Society of Chemistry.

Jiang, Tao, et al., "Research advances of 1—hexene process by ethylene trimerization," Oct. 2000, pp. 284-287, vol. 18, No. 5, Petrochemical Technology & Application.

Köhn, R. D., et al., "Olefin trimerization with 1,3,5-triazacydohexane complexes of chromium," INOR 278, 2 pages.

Köhn, Randolf D., et al., "1,3,5-Triazacyclohexane complexes of chromium as homogeneous model systems for the phillips catalyst," 2003, pp. 88-100, vol. 857, American Chemical Society.

Köhn, Randolf D., et al., "1,3,5-Triazacyclohexane complexes of chromium as homogeneous model systems for the phillips catalyst," pp. 147-155.

Köhn, Randolf D., et al., "Selective trimerization of a-olefins with triazacyclohexane complexes of chromium as catalysts," Angew. Chem. Int. Ed., 2000, pp. 4337-4339, vol. 39, No. 23, Wiley-VCH Verlag GmbH, D-69451 Weinheim.

Luo, He-Kuan, et al., "The effect of halide and the coordination geometry of chromium center in homogeneous catalyst system for ethylene trimerization," Journal of Molecular Catalysis A: Chemical, 2004, pp. 9-17, vol. 221, Elsevier B.V.

Mahomed, Hamdani, et al., "Ethylene trimerisation catalyst based on substituted cyclopentadienes," Applied Catalysis A: General, 2003, pp. 355-359, vol. 255, Elsevier B.V.

Manyik, R. M., et al., "A soluble chromium-based catalyst for ethylene trimerization and polymerization," Journal of Catalysis, 1977, pp. 197-209, vol. 47, Academic Press, Inc.

McGuinnes, David S., et al., "First Cr(III)—SNS complexes and their use as highly efficient catalysts for the trimerization of ethylene to 1-hexene," J. Am. Chem. Soc., 2003, pp. 5272-5273, vol. 125, No. 18, American Chemical Society.

McGuinnes, David S., et al., "Novel Cr-PNP complexes as catalysts for the trimerization of ethylene," Chem. Commun., 2003, pp. 334-335, The Royal Society of Chemistry.

Meijboom, Nicolaas, et al., "Organometallic chemistry of chromium(VI): synthesis of chromium(VI) alkyls and their precursors. X-ray crystal structure of the metallacycle Cr(NtBu)2{o-(CHSiMe3)2C6H4}," Organometallics, 1990, pp. 774-782, vol. 9, No. 3, American Chemical Society.

Mihan, Shahram, et al., "Triazacyclohexane complexes of chromium for selective trimerization," 1 page, INOR 114.

Monoi, Takashi, et al., "Silica-supported Cr[N(SiMe3)2]3/isobutylalumoxane catalyst for selective ethylene trimerization," Journal of Molecular Catalysis, 2002, pp. 135-141, vol. 187, Elsevier Science B.V.

Morgan, David H., et al., "The effect of aromatic ethers on the trimerisation of ethylene using a chromium catalyst and aryloxy ligands," Adv. Synth. Catal., 2003, pp. 939-942, vol. 345, Wiley-VCH Verlag GmbH & Co. KGaA, Weinheim.

Ninanalov, I. I., et al., "Equilibrium of the trimerization of ethylene into hexenes," Ref. Zh., Khim, Abstract No. 24B897, 1983, 2 pages, ACS.

Notice of Allowance dated Jul. 30, 2007 (14 pages), U.S. Appl. No. 10/783,737, filed Feb. 20, 2004.

Office Action dated Oct. 5, 2006 (6 pages), U.S. Appl. No. 10/783,737, filed Feb. 20, 2004.

Office Action dated Jan. 26, 2007 (25 pages), U.S. Appl. No. 10/783,737, filed Feb. 20, 2004.

Office Action dated May 24, 2005 (6 pages), U.S. Appl. No. 10/783,429, filed Feb. 20, 2004.

Office Action dated Aug. 31, 2005 (13 pages), U.S. Appl. No. 10/783,429, filed Feb. 20, 2004.

Office Action dated Jan. 18, 2006 (15 pages), U.S. Appl. No. 10/783,429, filed Feb. 20, 2004.

Office Action dated May 24, 2006 (8 pages), U.S. Appl. No. 10/783,429, filed Feb. 20, 2004.

Office Action dated Sep. 7, 2006 (4 pages), U.S. Appl. No. 10/783,429, filed Feb. 20, 2004.

Office Action dated Jan. 9, 2007 (13 pages), U.S. Appl. No. 10/783,429, filed Feb. 20, 2004.

Office Action dated Apr. 19, 2007 (8 pages), U.S. Appl. No. 10/783,429, filed Feb. 20, 2004.

Office Action dated Sep. 28, 2007 (8 pages), U.S. Appl. No. 10/783,429, filed Feb. 20, 2004.

Ranwell, A., et al., "Potential application of ionic liquids for olefin oligomerization," Sasol Technology R&D, Sasolburg, South Africa, 2002, pp. 147-160, American Chemical Society.

Rao, Guo-Ying, et al., "Coordination mode of the Cr(2-ethylhexanoate)3/triethylaluminurn/dimethylpyrrole/tetrachloroethane," 2003, pp. 80-82, vol. 30, No. 1, Journal of Beijing University of Chemical Technology, Beijing, China.

Reagen, W. K., "Chromium(II) and (III) pyrrolyl ethylene oligomerization catalysts. Synthesis and crystal structure of square planar Cr(NC4H4)4-2, and pentanuclear (Cr5(NC4H4)10(OC4H8)4)," Symposium on Novel Preparation and Conversion of Light Olefins presented before the division of Petroleum Chemistry, Inc., Sep. 10-15, 1989, pp. 583-588, American Chemical Society.

Sui, Junlong, et al., "Synthesis of 1—hexene by trimerization of ethylene," 2001, pp. 23-26, 43, vol. 18, No. 2, China Synthetic Resin and Plastics.

Tamura, Takao, "Recent trends in a -olefin manufacturing technology," Idemitsu Giho, 1995, pp. 266-269, vol. 38, No. 3.

Tobisch, Sven, et al., "Catalytic linear oligomerization of ethylene to higher a-olefins: insight into the origin of the selective generation of 1-hexene promoted by a cationic cyclopentadienyl-arene titanium active catalyst," Organometallics, 2003, pp. 5392-5405, vol. 22, No. 26, American Chemical Society.

Tobisch, Sven, et al., "Catalytic oligomerization of ethylene to higher linear a-olefins promoted by cationic group 4 cyclopentadienyl-arene active catalysts: a DFT investigation exploring the influence of electronic factors on the catalytic properties by modification of the hemilabile arene functionality," Organometallics, 2004, pp. 4077-4088, vol. 23, No. 17, American Chemical Society.

Tobisch, Sven, et al.,"Catalytic oligomerization of ethylene to higher linear a-olefins promoted by cationic group 4 [(n5-Cp-(CMe2-bridge)-Ph)M11(ethylene)2]+ (M = Ti, Zr, Hf) active catalysts: a density functional investigation of the influence of the metal on the catalytic activity and selectivity." J. Am. Chem. Soc., 2004, pp. 9059-9071, vol. 126, No. 29, American Chemical Society.

Tobisch, Sven, et al., "Catalytic oligomerization of ethylene to higher linear a-olefins promoted by cationic group 4 cyclopentadienyl-arene active catalysts: toward the computational design of zirconium- and hafnium-based ethylene trimerization catalysts," Organometallics, 2005, pp. 256-265, vol. 24, No. 2, American Chemical Society.

Van Rensburg, Werner Janse, et al., "A DFT study toward the mechanism of chromium-catalyzed ethylene trimerization," Organometallics, 2004, pp. 1207-1222, vol. 23, No. 6, American Chemical Society.

Wu, Tianzhi, et al., "Catalytic trimerization of ethylene by half-sandwich titanium complexes bearing a pendant ethereal group," Journal of Molecular Catalysis A: Chemical, 2004, pp. 227-229, vol. 214, Elsevier B.V.

Yang, Y., et al., "Roles of chloro compound in homogeneous [Cr(2-ethylhexanoate)3/2,5-dimethylpyrrole/triethylaluminum/chlorocompound] catalyst system for ethylene trimerization," Applied Catalysis A: General, 2000, pp. 29-38, vol. 193, Elsevier Science B.V.

Ye, Zhibin, et al., "A tandem catalytic system for the synthesis of ethylene—hex-1-ene copolymers from ethylene stock," Macromol. Rapid Commun., 2004, pp. 647-652, vol. 25, Wiley-VCH Verlag GmbH & Co. KGaA, Weinheim.

Yu, Zhi-Xiang, et al., "Why trimerization? Computational elucidation of the origin of selective trimerization of ethene catalyzed by [TaCl3(CH3)2] and an agostic-assisted hydride transfer mechanism," Angew. Chem. Int. Ed., 2003, pp. 808-811, vol. 42, No. 7, Wiley-VCH Verlag GmbH & Co. KGaA, Weinheim.

* cited by examiner

US 8,329,608 B2

METHODS OF PREPARATION OF AN OLEFIN OLIGOMERIZATION CATALYST

CROSS-REFERENCE TO RELATED APPLICATIONS

This is a Continuation Application claiming priority to U.S. patent application Ser. No. 10/783,429, filed Feb. 20, 2004 and entitled "Methods of Preparation of an Olefin Oligomerization Catalyst." This application is related to U.S. patent application Ser. No. 10/783,737, filed Feb. 20, 2004 and entitled "Methods of Preparation of an Olefin Oligomerization Catalyst," each of the above applications is hereby incorporated herein by reference in its entirety for all purposes.

FIELD OF THE INVENTION

The present invention relates to preparation of catalysts for use in a process for producing an olefin oligomer. More particularly, the present invention relates to preparing trimerization catalysts comprising a chromium-containing compound, a pyrrole-containing compound, a metal alkyl, and a halide-containing compound for use in a process for producing an alpha-olefin oligomer comprising 1-hexene from ethylene.

BACKGROUND OF THE INVENTION

Olefin oligomerization catalysts are known in the art, but sometimes lack selectivity to a desired product and also have a low product yield. Enhancements in preparation methods for oligomerization catalysts to improve productivity and selectivity to the desired product can reduce catalyst cost and improve economics.

SUMMARY OF THE INVENTION

Disclosed herein is a method of making a catalyst for use in oligomerizing an olefin, comprising a chromium-containing compound, a pyrrole-containing compound, a metal alkyl, a halide-containing compound, and optionally a solvent the method comprising abating all or a portion of water, acidic protons, or both from a composition comprising the chromium-containing compound, a composition comprising the pyrrole-containing compound, a composition comprising a non-metal halide-containing compound, a composition comprising the solvent, or combinations thereof prior to contact thereof with a composition comprising a metal halide-containing compound.

Further disclosed herein is a process for preparing a chromium-based catalyst, comprising bringing a pyrrole ring-containing compound, an alkyl aluminum compound, and a halogen-containing compound into contact with each other in a hydrocarbon solvent, halogenated hydrocarbon solvent or mixture thereof, and then bringing the mixed resultant solution into contact with the chromium compound, wherein water, acidic protons, or both are abated from the catalyst or a component thereof prior to or during preparation of the catalyst.

Further disclosed herein is a process for preparing a chromium-based catalyst, comprising bringing a chromium compound, a pyrrole ring-containing compound, an alkyl aluminum compound, and a halogen-containing compound into contact with each other in a hydrocarbon solvent, halogenated hydrocarbon solvent or mixture thereof in the absence of alpha-olefin under such a condition that the concentration of the chromium compound in the resultant mixed solution is about $1\times10^{-7}$ to 1 mol/liter, wherein water, acidic protons, or both are abated from the catalyst or a component thereof prior to or during preparation of the catalyst.

Further disclosed herein is a catalyst system for the oligomerization of olefins, the catalyst system including: a chromium source; a metal alkyl; and a halopyrrole ligand, wherein water, acidic protons, or both are abated from the catalyst system or a component thereof prior to or during formation of the catalyst.

Further disclosed herein is a method of producing 1-hexene including at least the step of trimerizing ethylene using a catalyst system comprising a combination of at least a chromium source, a metal alkyl and a halopyrrole ligand, wherein water, acidic protons, or both are abated from the catalyst system or a component thereof prior to or during formation of the catalyst.

Further disclosed herein is a multidentate mixed heteroatomic ligand for an oligomerization of olefins catalyst, which ligand includes at least three heteroatoms of which at least one is a sulfur atom wherein water or acidic protons, or both are abated from the catalyst system or a catalyst component.

Further disclosed herein is a mixed heteroatomic ligand for an oligomerization of olefins catalyst, which ligand includes at least three heteroatoms, of which at least one heteroatom is nitrogen and at least two heteroatoms are not the same wherein water or acidic protons, or both are abated from the catalyst system or a catalyst component.

DETAILED DESCRIPTION

Figure 1A:
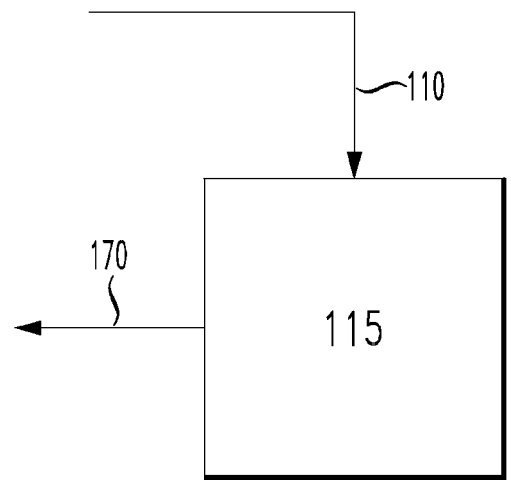
FIGS. 1A through 1D illustrate various embodiments of a method of preparing an oligomerization catalyst comprising bulk addition of catalyst components.

As used herein, a catalyst component includes a chromium-containing compound, a pyrrole-containing compound, a metal alkyl, a halide-containing compound, a solvent, or combinations thereof. In the various embodiments disclosed herein, contacting of catalyst components may occur in one or more contact zones. A contact zone is a zone in which the components are commingled and/or combined, and thereby contacted. The contact zone may be disposed in a vessel, e.g. a storage tank, tote, container, mixing vessel, reactor, etc.; a length of pipe, e.g. a tee, inlet, injection port, or header for combining component feed lines into a common line; or any other suitable apparatus for bringing the components into contact. As used herein, the terms contacted and combined refer to any addition sequence, order, or concentration for contacting or combining two or more catalyst components. The term added to refers to a first catalyst component added, e.g., poured, into a second catalyst component. Where a first catalyst component is added to a second catalyst component, the initial concentration, or molar ratio, of the first catalyst component compared to the second catalyst component typically is relatively small and increases over the duration of the addition. In some embodiments, contacting of components may occur in one or more upstream contact zone(s) prior to further contacting with other catalyst component(s) in one or more downstream contact zone(s). Where a plurality of contact zones are employed, contacting may occur simultaneously across the contact zones, sequentially across the contact zones, or both, as is suitable for a given embodiment. Contacting may be carried out in a batch or continuous process, as is suitable for a given embodiment.

In embodiments utilizing a vessel for contacting the components, the components may be optionally mixed by a mixer disposed in the vessel and the formed mixture may then be removed for subsequent processing. In embodiments utilizing a tee or other means for combing lines such as a header, an optional in-line mixer may be placed in the commingled catalyst feed line to ensure that adequate contacting of the combined components takes place, and the mixture is thus formed as it passes through the commingled feed line. Where a method of making a catalyst recites contact or combination of catalyst components, such may be carried out by contacting or combining all or a portion of such components in various embodiments.

As used herein, a composition comprising a catalyst component includes the catalyst component alone or in combination with one or more additional compounds, solvents, or both. None, some, or all of the contacting steps may be carried out in the presence of a solvent (sometimes referred to as an optional solvent), which may be introduced to a contact zone via inclusion with one or more compositions comprising a catalyst component or may be introduced separately to a contact zone, for example in a solvent line or as an initial charge to a contact zone.

Disclosed herein is a method of making a catalyst comprising a chromium-containing compound, a pyrrole-containing compound, a metal alkyl, a halide-containing compound, and optionally a solvent for use in oligomerizing an olefin, wherein a composition comprising the chromium-containing compound is contacted in a contact zone with a composition comprising the metal alkyl. In FIG. 1, four embodiments for contacting the composition comprising the chromium-containing compound with the composition comprising the metal alkyl in a contact zone are illustrated. FIGS. 1A through 1D are included as illustrative representations of embodiments of the present disclosure and do not limit the disclosure.

In an embodiment as illustrated in FIG. 1A, the composition comprising the metal alkyl may be disposed in contact zone 115 and the composition comprising the chromium-containing compound may be contacted with or added to the composition comprising the metal alkyl present in contact zone 115 via line 110. The final catalyst composition may be recovered as a product via line 170. The composition comprising the chromium-containing compound in line 110 may further comprise the pyrrole-containing compound, a non-metal halide-containing compound, the solvent, or combinations thereof. The composition comprising the chromium-containing compound may also comprise an amount of non-halide metal alkyl to abate undesired water, acidic protons, or both, as disclosed in more detail herein. The final catalyst composition may be further dilute with a solvent (which may not be identical to the catalyst preparation solvent) prior to use in the oligomerization reaction.

The composition comprising the metal alkyl present in contact zone 115, may comprise the pyrrole-containing compound, the halide-containing compound, the solvent, or combinations thereof. The halide-containing compound may be a metal halide, non-metal halide, or combinations thereof. The composition comprising the metal alkyl may also comprise a metal alkyl halide, a non-halide metal alkyl, a non-metal halide, a metal halide, or combinations thereof. The metal alkyl halide in this and other embodiments may comprise diethylaluminum chloride (DEAC) and the non-halide metal alkyl may comprise triethyl aluminum (TEA). In an embodiment the metal alkyl may be the halide-containing compound, e.g. DEAC is the halide-containing compound and the metal alkyl.

Figure 1B:
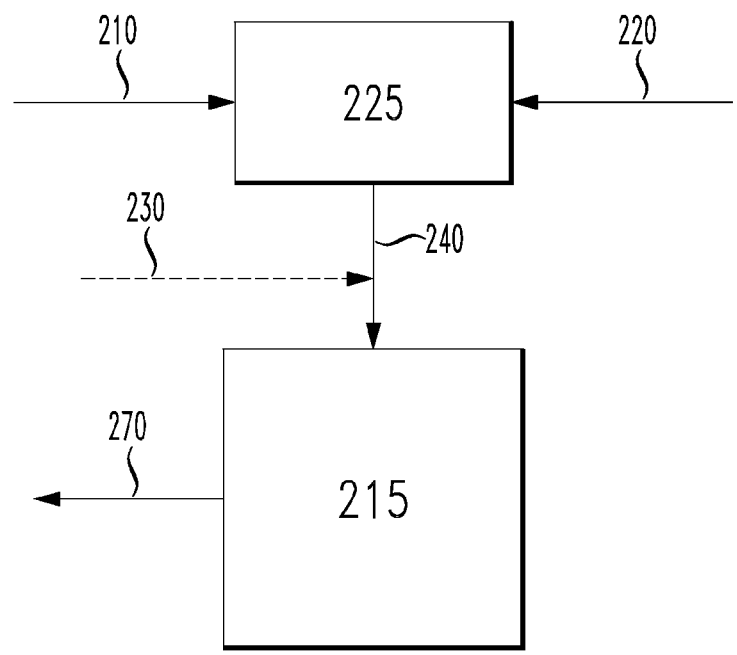

In an embodiment as illustrated in FIG. 1B, a pyrrole-chromium mixture may be formed in contact zone 225 by contacting a composition comprising the pyrrole-containing compound fed to contact zone 225 via line 220 and the composition comprising the chromium-containing compound fed to contact zone 225 via line 210, which may occur about instantaneously or over a first period of time of from about 1 minute to about 12 hours, alternatively from about 1 minute to about 6 hours, alternatively from about 1 minute to about 3 hours, alternatively from about 1 hour to about 2 hours. Introduction of the composition comprising the chromium-containing compound and the composition comprising the pyrrole-containing compound to contact zone 225 may be sequential (e.g. chromium followed by pyrrole or vice-versa) or simultaneous. Once the pyrrole-chromium mixture has been contacted in contact zone 225 the pyrrole-chromium mixture from contact zone 225 may be contacted with or added to the composition comprising the metal alkyl present in contact zone 215 via line 240, which may occur about instantaneously or over a second period of time of from about 1 minute to about 12 hours, alternatively from about 1 minute to about 6 hours, alternatively from about 1 minute to about 3 hours, to form the final catalyst product in contact zone 215. The final catalyst product may be withdrawn from contact zone 215 via line 270. The final catalyst composition may be further dilute with a solvent (which may not be identical to the catalyst preparation solvent) prior to use in the oligomerization reaction.

The composition comprising the pyrrole-containing compound in line 220 and the composition comprising the chromium-containing compound in line 210 may be contacted, e.g., over the first period of time, at an about constant pyrrole to chromium (Py:Cr) molar ratio or alternatively at a variable Py:Cr molar ratio to form the pyrrole-chromium mixture in contact zone 225. The pyrrole-chromium mixture in contact zone 225 may then be contacted with or added to, e.g., over the second period of time, the metal alkyl present in contact zone 215 via line 240, or alternatively already present in contact zone 215, at an about constant Py:Cr molar ratio, for example in the range of from about 1.0:1 to about 4.0:1. Alternatively, the pyrrole-chromium mixture in contact zone 225 may then be contacted with or added to, e.g., over the second period of time, the metal alkyl present in contact zone 215 via line 240 at a variable Py:Cr molar ratio. In an embodiment the variable Py:Cr molar ratio is decreasing over the second period of time where a decreasing Py:Cr molar ratio refers to a general decreasing trend in the molar ratio from the start of the addition sequence to the finish and occasional increases in the ratio within the overall decreasing trend are acceptable. In an embodiment a decreasing trend of the Py:Cr refers to the specific situation where the ending Py:Cr ratio is less than the beginning Py:Cr ratio. In an embodiment, an initial Py:Cr molar ratio at the start of the addition may be greater than the final Py:Cr molar ratio of the catalyst; and an ending Py:Cr molar ratio at the end of the addition may be less than the final Py:Cr molar ratio of the catalyst. In an embodiment, the final Py:Cr molar ratio of the catalyst may be in a range of from about 1.0:1 to about 4.0:1; the initial Py:Cr molar ratio may be greater than about 6:1, alternatively greater than about 20:1, alternatively greater than about 40:1, alternatively greater than about 60:1; and the ending Py:Cr molar ratio may be greater than or equal to about 0, alternatively greater than or equal to about 0.1:1, alternatively greater than or equal to about 0.3:1, and alternatively greater than or equal to about 0.6:1. In an embodiment, the initial Py:Cr molar ratio is about twice the final Py:Cr molar ratio of the catalyst during a first about one-half of the addition and the ending Py:Cr molar ratio is about 0 during a second about one-half of the addition, wherein the final Py:Cr molar ratio of the catalyst is in a range of from about 1.0:1 to about 4.0:1. Introduction of a pyrrole-containing compound and a chromium-containing compound in a contact zone (e.g., formation of a Py:Cr mixture) as disclosed in various embodiments may be carried out as disclosed in this paragraph, including but not limited to the embodiments shown in FIGS. 1D, 2C, 2D, 3B, and 4A-E.

The composition comprising the chromium-containing compound in line 210 may comprise a non-metal halide-containing compound, the solvent, or combinations thereof. The composition comprising the pyrrole-containing compound in line 220 may comprise a non-metal halide-containing compound, the solvent, or combinations thereof. The composition comprising the chromium-containing compound in line 210, the composition comprising the pyrrole-containing compound in line 220, or both may also comprise an amount of non-halide metal alkyl to abate undesired water, acidic protons, or both as disclosed herein. Alternatively, the non-halide metal alkyl may be contacted with or added to the pyrrole-chromium mixture, for example in line 240 via line 230, in contact zone 225 (not shown), or both, to abate undesired water, acidic protons, or both. The composition comprising the metal alkyl present in contact zone 215, may comprise the halide-containing compound, the solvent, or combinations thereof. The composition comprising the metal alkyl may also comprise a metal alkyl halide, a non-halide metal alkyl, a metal halide, non-metal halide, or combinations thereof.

Figure 1C:
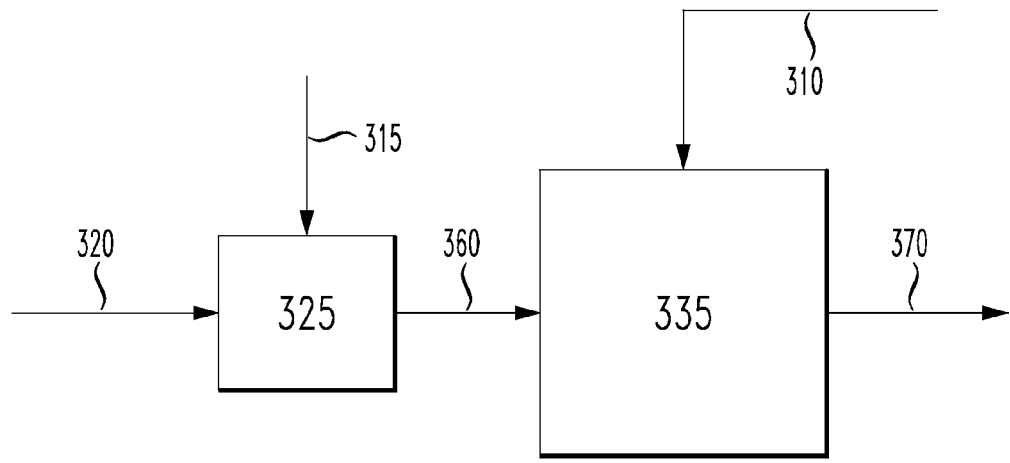

In an embodiment as shown in FIG. 1C, a pyrrole-metal alkyl mixture may be formed in contact zone 325 by contacting the composition comprising the pyrrole-containing compound fed to contact zone 325 via line 320 with the composition comprising the metal alkyl fed to contact zone 325 via line 315 which may occur about instantaneously or over a first period of time. Addition of the composition comprising the pyrrole-containing compound and the composition comprising the metal alkyl to contact zone 325 may be sequential (e.g. pyrrole followed by metal alkyl or vice-versa) or simultaneous. Once the pyrrole-metal alkyl mixture has been contacted in contact zone 325 the pyrrole-metal alkyl mixture from contact zone 325 may be disposed via line 360 in contact zone 335. The composition comprising the chromium-containing compound may then be contacted with or added to contact zone 335 via line 310, which may occur about instantaneously or over a second period of time. The composition comprising the chromium-containing compound is thus contacted with or added to the pyrrole-metal alkyl mixture present in contact zone 335, to form the final catalyst product in contact zone 335. Addition of the composition comprising the pyrrole-metal alkyl mixture and the composition comprising the chromium-containing compound to contact zone 335 may be sequential (e.g. pyrrole-metal alkyl followed by the chromium containing compound or vice-versa) or simultaneous. The final catalyst product may be withdrawn from contact zone 335 via line 370. The final catalyst composition may be further diluted with a solvent (which may not be identical to the catalyst preparation solvent) prior to use in the oligomerization reaction.

Although the embodiment shown in FIG. 1C shows two contact zones being used to perform the addition sequences, the addition sequences could alternatively be performed in a single contact zone, for example, in contact zone 325. In this embodiment, the composition comprising the metal alkyl may first be placed in the contact zone. In a second step the composition comprising the pyrrole-containing compound may be contacted with or added to the composition comprising the metal alkyl present in the contact zone (or visa-versa) to adequately contact and form the pyrrole-metal alkyl mixture. In a third step, the composition containing the chromium-containing compound may be contacted with or added to the pyrrole-metal alkyl mixture to form the final catalyst product.

The composition comprising the chromium-containing compound in line 310 may comprise a non-metal halide-containing compound, the solvent, or combinations thereof. The composition comprising the pyrrole-containing compound in line 320 may comprise a non-metal halide-containing compound, the solvent, or combinations thereof. The composition comprising the chromium-containing compound in line 310, the composition comprising the pyrrole-containing compound in line 320, or both may comprise an amount of non-halide metal alkyl to abate undesired water, acidic protons, or both. The composition comprising the metal alkyl in line 315, may comprise the halide-containing compound, the solvent, or combinations thereof. The composition comprising the metal alkyl may also comprise a metal alkyl halide, a non-halide metal alkyl, a metal halide, non-metal halide, or combinations thereof.

Figure 1D:
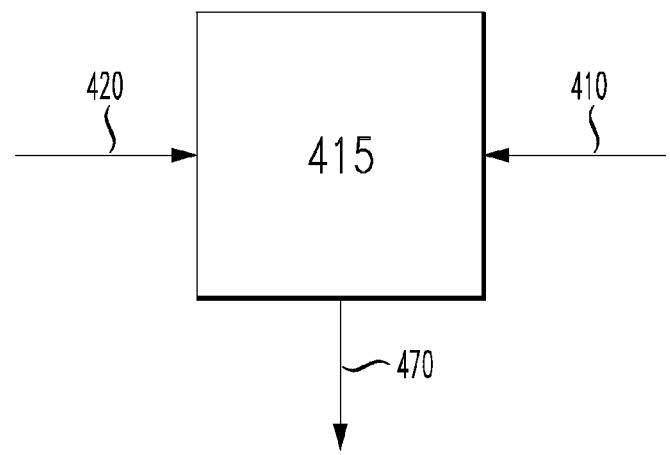

In an embodiment as shown in FIG. 1D, a composition comprising the pyrrole-containing compound in line 420 and a composition comprising the chromium-containing compound in line 410 may be simultaneously contacted with or added to, which may occur about instantaneously or over a period of time, with a composition comprising the metal alkyl present in contact zone 415, and a final catalyst product may be withdrawn from contact zone 415 via line 470. The final catalyst composition may be further diluted with a solvent (which may not be identical to the catalyst preparation solvent) prior to use in the oligomerization reaction. The composition comprising the chromium-containing compound and the composition comprising the pyrrole-containing compound may be contacted with or added to the composition comprising the metal alkyl at Py:Cr molar ratios described previously.

The composition comprising the chromium-containing compound in line 410 may comprise a non-metal halide-containing compound, the solvent, or combinations thereof. The composition comprising the pyrrole-containing compound in line 420 may comprise a non-metal halide-containing compound, the solvent, or combinations thereof. In the embodiment shown in FIG. 1D, the composition comprising the metal alkyl in contact zone 415, may comprise the halide-containing compound, the solvent, or combinations thereof, each added to contact zone 415 through various input lines not shown in FIG. 1D. The composition comprising the metal alkyl may also comprise a metal alkyl halide, a non-halide metal alkyl, a metal halide, non-metal halide, or combinations thereof. The composition comprising the chromium-containing compound in line 410, the composition comprising the pyrrole-containing compound in line 420, or both may comprise an amount of non-halide metal alkyl to abate undesired water, acidic protons, or both.

Further disclosed herein is a method of making a catalyst comprising abating all or a portion of water, acidic protons, or both from a composition comprising the chromium-containing compound, a composition comprising the pyrrole-containing compound, a composition comprising the non-metal halide-containing compound, a composition comprising the solvent, or combinations thereof prior to contact thereof with a composition comprising the metal halide-containing compound. Abating water, acidic protons, or both may include neutralizing acidic protons; physically removing water; physically removing acidic protons; chemically binding or reacting free water such that the water is no longer free; or combinations thereof. The amount of water, acid protons, or both removed from the catalyst component may be determined using known methods, for example infrared analysis to determine water content.

In embodiments to prepare a catalyst, one or more of the catalyst components may contain water, for example the composition comprising the chromium-containing compound. Water may be present in a catalyst compound, for example as a contaminant or as a co-product produced during the preparation of the catalyst compound. For example, water may be co-produced during preparation of the chromium-containing compound, and such water may complex with the chromium. Acidic protons may also be present, for example carboxylic acid (e.g., ethylhexanoic acid) remaining from production of the chromium-containing compound (e.g., chromium tris(2-ethylhexanoate)). This free water as well as acid present in the chromium source can subsequently react with a metal halide present in the catalyst, for example the metal alkyl halide such as DEAC, to form corrosive compounds, e.g. hydrogen halide compound (e.g. hydrochloric acid). Such compounds may cause corrosion in downstream equipment over time, in particular when heated, for example in downstream fractionation facilities. Accordingly, it may be desirable to abate water, acidic protons, or both, when making the catalyst to prevent downstream formation of potentially corrosive by-products.

Furthermore, in embodiments of a method of preparing a catalyst, impurities in the catalyst components can participate in unwanted side reactions leading to the formation of precipitates. These precipitates may to lead to further unwanted reactions, for example polymer formation in the trimerization of ethylene to 1-hexene. Water may be an initiator of the precipitation reactions and therefore may be desirably abated from the catalyst components to improve selectivity to 1-hexene. Abating water, acidic protons, or both may also have beneficial impact on catalyst efficiency, even where corrosive compounds are produced. For example, in an embodiment, water is abated from one or more catalyst components by contact thereof with a corrosive abatement compound such as a halide-containing compound, which reacts with and abates the water. Reactions of water with a corrosive abatement compound such as a halide-containing compound may produce a corrosive compound, e.g., HCl, and such should be taken into account in the overall design of the system. Examples of suitable halide-containing compounds for reaction with water include a metal halide, a metal alkyl halide, a non-halide metal alkyl and a metal halide, a non-metal halide, or combinations thereof. The use of a halide-containing compound to abate water may be used in place of or in addition to other water abatement embodiments disclosed herein such as the use of a non-halide metal alkyl to abate water.

In an embodiment, water, acidic protons, or both may be abated by pre-contacting one or more catalyst components with a non-corrosive abatement compound, which is a compound that does not form a corrosive compound such as a hydrogen halide compound upon contact with the water, acidic protons, or both. Non-corrosive abatement compounds include, for example, a non-halide metal alkyl such as TEA. Corrosive abatement compounds are compounds that can form a corrosive compound upon contact with water, acidic protons or both such as (i) a metal alkyl halide, (ii) a metal halide and a metal alkyl, and (iii) a non-metal halide and a metal alkyl. The corrosive abatement compounds also include any other combination of compounds that form a corrosive compound upon contact with water, acidic proton, or both.

In an embodiment, one or more catalyst components such as a composition comprising the chromium-containing compound, a composition comprising the pyrrole-containing compound, a non-metal halide-containing compound, a solvent, or combinations thereof, are contacted with a non-halide metal alkyl to abate water, acidic protons, or both. The non-halide metal alkyl can react with free water, acid protons, or both contained in the catalyst component(s) when pre-contacted to abate water, acidic protons, or both. The non-halide metal alkyl may be pre-mixed in a contact zone with the one or more catalyst components. The pre-mix may be made by either adding the non-halide metal alkyl to the catalyst component(s) or vice versa, and in an embodiment, the pre-mix may be made by adding the non-halide metal alkyl to the catalyst component(s). These additions can be made in various ratios as described below.

In an embodiment, the non-halide metal alkyl in added to or contacted with a composition comprising the chromium-containing compound. Given that the chromium may react with the non-halide metal alkyl to form a gel, it may be desirable to maintain a low concentration of non-halide metal alkyl by adding it to the composition comprising the chromium-containing compound, so that there may only be an amount available to react with the water and acid. Conversely, with a high concentration of non-halide metal alkyl, such as can occur when adding the composition comprising the chromium-containing compound to the non-halide metal alkyl, more non-halide metal alkyl would be available to react with the chromium (and thereby form a gel) after the water and acid were removed.

In each embodiment, the water or acid abating substance (e.g., a non-halide metal alkyl) may be contacted with or added to one or more catalyst components in an amount effective to abate substantially all free/available water, acidic protons, or both from some or all of the components contacted with the non-halide metal alkyl. In an embodiment, the amount of non-halide metal alkyl contacted with or added to such components is small relative to the amount of the catalyst components to which it is being contacted with or added to. In an embodiment, the portion of the non-halide metal alkyl contacted with or added to a catalyst component(s) may be less than or equal to about 30 weight percent of the catalyst component(s) to which it is contacted with or added to; alternatively less than about 20 weight percent of the catalyst component(s) to which it is contacted with or added to; alternatively less than about 10 weight percent of the catalyst component(s) to which it is contacted with or added to; alternatively less than about 5 weight percent of the catalyst component(s) to which it is contacted with or added to. In an embodiment, the portion of the non-halide metal alkyl contacted with or added to a catalyst component(s) may be less than or equal to about 120 mole percent of the catalyst component(s) to which it is contacted with or added to; alternatively less than about 80 mole percent of the catalyst component(s) to which it is contacted with or added to; alternatively less than about 40 mole percent of the catalyst component(s) to which it is contacted with or added to; alternatively less than about 20 mole percent of the catalyst component(s) to which it is contacted with or added to. The non-halide metal alkyl may be contacted with or added to a catalyst component(s) in an amount such that the non-halide metal alkyl to catalyst component(s) molar ratio may be less than about 1.5:1, alternatively less than about 1.2:1, alternatively less than about 1:1. The non-halide metal alkyl may be contacted with or added to a catalyst component(s) in a molar ratio sufficient to abate at least about 25% of the water, acidic protons, or both associated with the catalyst component(s) present in the pre-contacting contact zone; alternatively at least about 90% of the water, acidic protons, or both associated with the catalyst component(s) present in the pre-contacting contact zone; alternatively at least about 100% of the water, acidic protons, or both associated with the catalyst component(s) present in the pre-contacting contact zone; alternatively in an amount that may be at least about 10% in excess of an amount sufficient to abate at least about 100% of the water, acidic protons, or both associated with the catalyst component(s) present in the pre-contacting contact zone; alternatively in an amount that may be at least about 20% in excess of an amount sufficient to abate at least about 100% of the water, acidic protons, or both associated with the catalyst component(s) present in the pre-contacting contact zone; alternatively in an amount that may be at least about 30% in excess of an amount sufficient to abate at least about 100% of the water, acidic protons, or both associated with the catalyst component(s) present in the pre-contacting contact zone; alternatively in an amount that may be at least about 100% in excess of an amount sufficient to abate at least about 100% of the water, acidic protons, or both associated with the catalyst component(s) present in the pre-contacting contact zone; or alternatively in an amount that may be at least about 200% in excess of an amount sufficient to abate at least about 100% of the water, acidic protons, or both associated with the catalyst component(s) present in the pre-contacting contact zone.

Upon abatement of water, acidic protons, or both from one or more catalyst components, such abated catalyst components may be stored until needed for preparation of a catalyst composition. Such storage may or may not be in the presence of a solvent. The pre-mix comprising a portion of non-halide metal alkyl and one or more abated catalyst component(s) may then be contacted with the remaining catalyst components including the metal alkyl halide to form the final catalyst product. The remaining catalyst components may also comprise additional non-halide metal alkyl to comprise the total non-halide metal alkyl composition in the final catalyst. In an embodiment, the additional non-halide metal alkyl may be the same as that used in the pre-mix. Alternatively, the additional non-halide metal alkyl may be different from that used in the pre-mix.

FIGS. 2A-2D represent various embodiments for abating water, acidic protons, or both in the composition comprising the chromium-containing compound, the composition comprising the pyrrole-containing compound, or both prior to contact with the composition comprising a metal halide-containing compound. FIGS. 2A through 2D are included as illustrative representations of embodiments of the present disclosure and do not limit the disclosure. Furthermore, various embodiments for abating water, acidic protons, or both may be combined to increase overall effectiveness.

The composition comprising a chromium-containing compound may be contacted with the non-halide metal alkyl to form a mixture prior to contacting the mixture with the remaining catalyst components. In an embodiment shown in FIG. 2A a composition containing the chromium-containing compound may be disposed in contact zone 510, the placement of which may take place via input line 505. The composition in contact zone 510 may optionally contain solvent, other catalyst components, or combinations thereof, provided that contact zone 510 does not comprise (i) a metal alkyl halide, (ii) a metal halide and a metal alkyl, or (iii) a non-metal halide and a metal alkyl. Non-halide metal alkyl, optionally in solvent, may be added to the composition containing a chromium-containing compound in contact zone 510 via line 530. The non-halide metal alkyl may be added in an amount less than or equal to about 30 weight percent of the composition containing the chromium-containing compound to which it is added or in other amounts as disclosed herein.

The resultant mixture in contact zone 510 may then be passed from contact zone 510 via line 511 and optionally fed into a filter 512, comprising dry (free of any water) filter medium, for filtering any precipitate that may have formed from the mixture. The precipitate may be filtered and the filtrate may be passed via line 513 into contact zone 515 for contacting with the remaining catalyst components including a composition comprising the metal alkyl, the pyrrole-containing compound, the halide-containing compound (e.g., a metal halide or non-metal halide), the solvent, any remaining non-halide metal alkyl, metal alkyl halide, or combinations thereof, which may be placed into contact zone 515 via various input lines not shown in FIG. 2A. A catalyst product may then be withdrawn from contact zone 515 via line 570. Where filtering is omitted, the remaining catalyst components may be alternatively contacted in contact zone 510.

The composition comprising a pyrrole-containing compound may be contacted with the non-halide metal alkyl to form a mixture prior to contacting the mixture with the remaining catalyst components. In an embodiment shown in FIG. 2B a composition comprising a pyrrole-containing compound may be disposed in contact zone 620 via input line 607. The composition in contact zone 620 may optionally contain solvent, other catalyst components, or combinations thereof, provided that contact zone 620 does not comprise (i) a metal alkyl halide, (ii) a metal halide and a metal alkyl, or (iii) a non-metal halide and a metal alkyl. Non-halide metal alkyl, which may be in solvent, may be added to the composition containing a pyrrole-containing compound in contact zone 620 via line 630. The non-halide metal alkyl may be added in an amount less than or equal to about 10 weight percent of the composition containing the pyrrole-containing compound to which it is added or in other amounts as disclosed herein.

The resultant mixture in contact zone 620 may then be passed from contact zone 620 via line 621 and optionally filtered (not shown) to remove any precipitate that may have formed in the mixture. The resultant mixture may then be fed into contact zone 615 for contacting with the remaining catalyst components including a composition comprising the metal alkyl, the chromium-containing compound, the halide-containing compound (e.g., a metal halide or non-metal halide), the solvent, any remaining non-halide metal alkyl, metal alkyl halide, or combinations thereof, which may be placed into contact zone 615 via various input lines not shown in FIG. 2B. A catalyst product may then be withdrawn from contact zone 615 via line 670. Where filtering is omitted, the remaining catalyst components may be alternatively contacted in contact zone 620 via various input lines not shown in FIG. 2B.

Figure 2A:
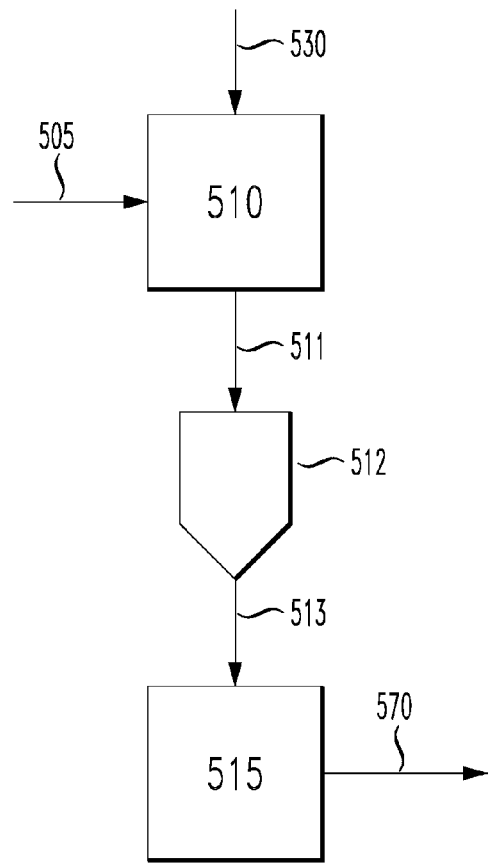
FIGS. 2A through 2D illustrate various embodiments of a method for abating water in the preparing of an oligomerization catalyst.
Figure 2B:
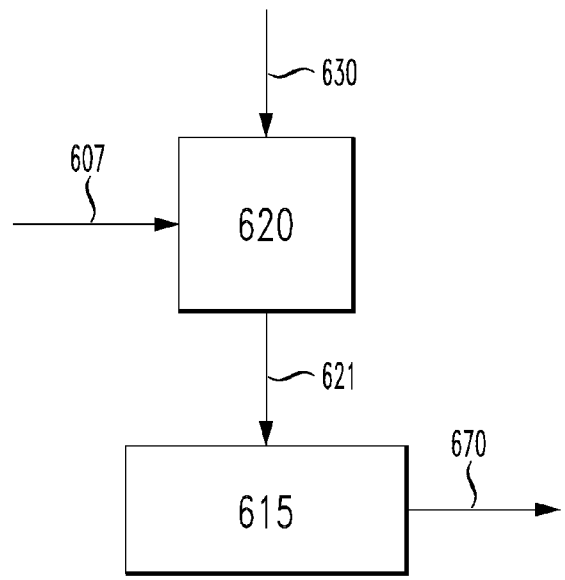
Figure 2C:
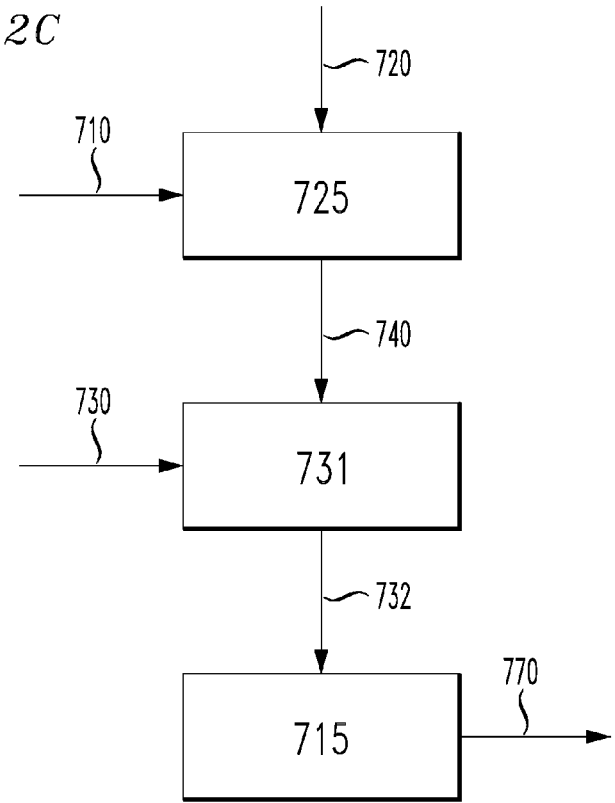

The composition comprising the chromium containing compound may be contacted with the composition comprising the pyrrole-containing compound to form a mixture prior to contacting the mixture with the non-halide metal alkyl. In an embodiment as illustrated in FIG. 2C, a pyrrole-chromium mixture may be formed in contact zone 725 by contacting a composition comprising the pyrrole-containing compound fed to contact zone 725 via line 720 and the composition comprising the chromium-containing compound fed to contact zone 725 via line 710, which may occur about instantaneously or over a first period of time. Feeding of the composition comprising the chromium-containing compound and the composition comprising the pyrrole-containing compound to contact zone 725 may be sequential (e.g. chromium followed by pyrrole or vice-versa) or simultaneous and at constant or varying Py:Cr ratios as disclosed previously. Once the pyrrole-chromium mixture has been contacted in contact zone 725 the pyrrole-chromium mixture from contact zone 725 may be placed in contact zone 731 via line 740. The pyrrole-chromium mixture may optionally contain solvent, other catalyst components, or combinations thereof, but does not comprise (i) a metal alkyl halide, (ii) a metal halide and a metal alkyl, or (iii) a non-metal halide and a metal alkyl. Non-halide metal alkyl, which may be in solvent, may be added to the pyrrole-chromium mixture in contact zone 731 via line 730. The non-halide metal alkyl may be added in an amount less than or equal to about 10 weight percent of the pyrrole-chromium mixture to which it is added or in other amounts as disclosed herein. Although not shown in FIG. 2C, contact zone 725 and contact zone 731 may be the same contact zone providing that the addition sequence as described above remains the same.

The resultant mixture in contact zone 731 may then be passed from contact zone 731 via line 732 and may optionally be filtered (not shown) to remove any precipitate that may have formed in the mixture. The mixture may be fed into contact zone 715 for contacting with the remaining catalyst components including a composition comprising the metal alkyl, the halide-containing compound (e.g., a metal halide or non-metal halide), the solvent, any remaining non-halide metal alkyl, metal alkyl halide, or combinations thereof, which may be placed into contact zone 715 via various input lines not shown in FIG. 2C. A catalyst product may then be withdrawn from contact zone 715 via line 770 and may optionally be filtered in a filter (not shown). Where filtering is omitted, remaining catalyst components may be alternatively contacted in contact zone 725 or 731.

The composition comprising a chromium-containing compound may be contacted with the non-halide metal alkyl to form a first mixture; the composition comprising a pyrrole-containing compound may be contacted with the non-halide metal alkyl to form a second mixture; and the first and second mixtures may be contacted with the remaining catalyst components. In an embodiment shown in FIG. 2D a composition containing a chromium-containing compound may be disposed in contact zone 810, the placement of which takes place via input line 805. The composition in contact zone 810 may optionally contain solvent, other catalyst components, or combinations thereof, but contact zone 810 does not comprise (i) a metal alkyl halide, (ii) a metal halide and a metal alkyl, or (iii) a non-metal halide and a metal alkyl. Non-halide metal alkyl, which may be in solvent, may be added to the composition containing a chromium-containing compound in contact zone 810 via line 830 forming a first mixture. The non-halide metal alkyl may be added in an amount less than or equal to about 10 weight percent of the composition containing the chromium-containing compound to which it is added or in other amounts as disclosed herein.

A second mixture can be formed in contact zone 820. The composition comprising a pyrrole-containing compound may be disposed in contact zone 820, the placement of which takes place via input line 807. The composition comprising a pyrrole-containing compound in contact zone 820 may optionally contain solvent, other catalyst components, or combinations thereof, but does not comprise (i) a metal alkyl halide, (ii) a metal halide and a metal alkyl, or (iii) a non-metal halide and a metal alkyl. Non-halide metal alkyl, which may be in solvent, may be added to the composition containing a pyrrole-containing compound in contact zone 820 via line 831 forming the second mixture. The non-halide metal alkyl may be added in an amount less than or equal to about 10 weight percent of the composition containing the pyrrole-containing compound to which it is added or in other amounts as disclosed herein.

The first mixture, second mixture, or both may optionally be filtered (not shown) to remove any precipitate that may have formed in the mixtures. Optionally, either the first, second, or both mixtures may be stored. The first and second mixtures may then be fed into contact zone 815 via lines 811 and 821, respectively for contacting with the remaining catalyst components including the composition comprising metal halide. Alternatively, although not shown in FIG. 2D the first and second mixtures may be contacted separately in another contact zone prior to being fed via a commingled feed line into contact zone 815, and such commingled feed line may be optionally filtered to remove any precipitate that may have formed. Contact zone 815 initially may be comprised of a composition comprising the metal alkyl, a halide-containing compound (e.g., a metal halide or non-metal halide), a solvent, the remaining non-halide metal alkyl, metal alkyl halide, or combinations thereof, all of which have been placed into contact zone 815 via various input lines not shown in FIG. 2D. A catalyst product may then be withdrawn from contact zone 815 via line 870 and optionally filtered (filter not shown). In alternative embodiments, remaining catalyst components may be contacted in contact zone 810 or 820.

Figure 2D:
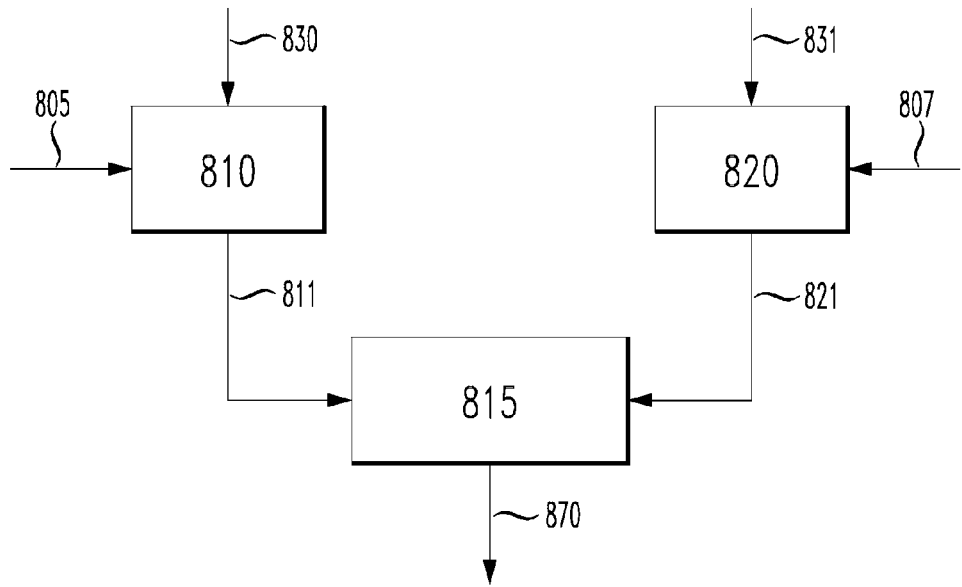

The addition of the composition comprising the pyrrole-containing compound and the composition comprising the chromium-containing compound as shown in FIGS. 2C and 2D may be made in constant or varying Py:Cr ratios as disclosed previously.

Water may be removed from the chromium-containing compound prior to contact with the metal halide-containing compound according to various water abatement embodiment disclosed herein. In an embodiment, the chromium-containing catalyst feedstock may be contacted with an azeotropic solvent such as an aromatic compound, paraffin solvent, chlorinated solvent, other solvent, or mixture of solvents capable of forming an azeotrope with water. The azeotropic solvent, the chromium-containing compound, and any water present form a solution and the solution may be subjected to an azeotropic distillation to remove the water, wherein the solvent-water azeotrope is a lower boiling component. Optionally, the solvent used to remove water by azeotropic distillation may be recovered after the azeotropic distillation. In an embodiment, the azeotropic solvent used to remove water using azeotropic distillation may comprise ethylbenzene, benzene, meta-xylene, ortho-xylene, para-xylene, mixed xylenes, toluene, octane, nonane, heptane, hexane, mixed hexanes, cyclohexane, carbon tetrachloride, chloroform, dichloromethane, 1,1,2 trichloroethane, or combinations thereof. The amount of water removed from a catalyst component by various abatement methods may be monitored using known analytical methods such as infrared analysis.

Figure 3A:
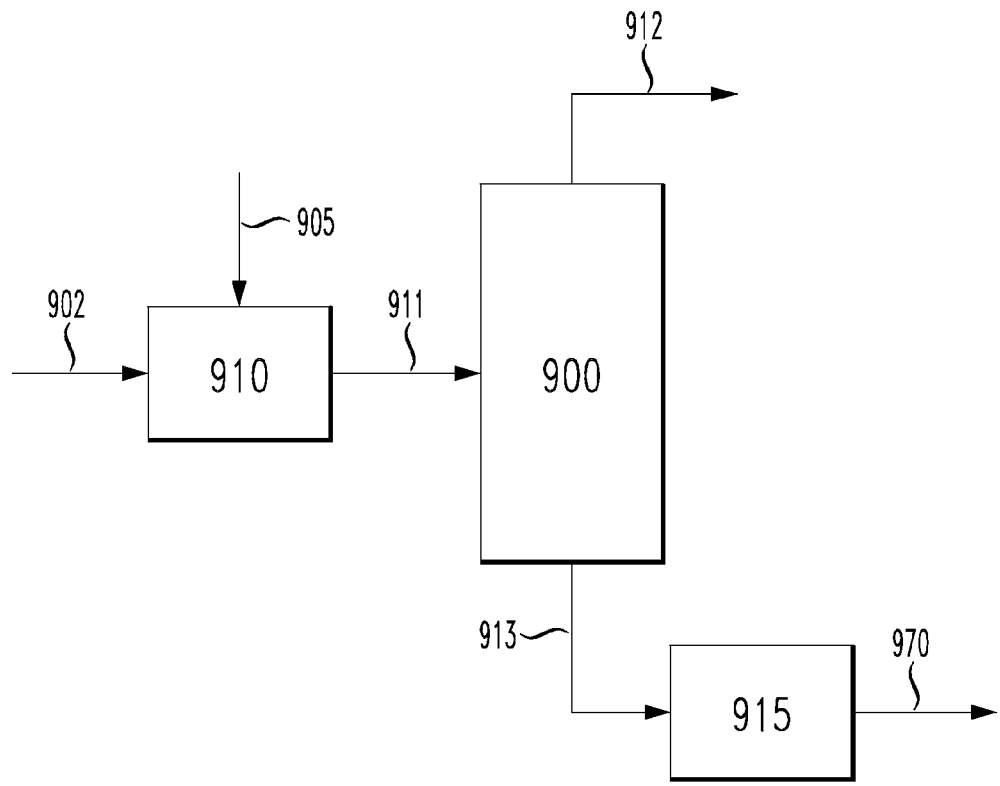
FIGS. 3A through 3B illustrate various embodiments of a method for abating water in the preparing of an oligomerization catalyst.

In an embodiment shown in FIG. 3A a composition containing a chromium-containing compound may be disposed in contact zone 910, the placement of which takes place via an input line 905. The composition in contact zone 910 may optionally contain solvent, other catalyst components, or combinations thereof, but contact zone 910 does not comprise (i) a metal alkyl halide, (ii) a metal halide and a metal alkyl, or (iii) a non-metal halide and a metal alkyl. An azeotropic solvent, e.g., a composition comprising an aromatic compound such as ethylbenzene, may be added to the composition containing a chromium-containing compound in contact zone 910 via line 902 or directly added to separator 900. The azeotropic solvent may be added in an amount effective to form an azeotropic solution with the chromium-containing compound. In an embodiment, the azeotropic solvent may be added in an amount from about 0.5 to about 1000 times the weight of the composition containing the chromium-containing compound to which it is added, alternatively from about 0.5 to about 500 times the weight, alternatively from about 0.5 to about 100 times the weight, alternatively from about 0.5 to about 50 times the weight, alternatively from about 0.5 to about 25 times the weight, alternatively from about 0.5 to about 15 times the weight. The resultant azeotropic solution in contact zone 910 may then be passed from contact zone 910 via line 911 and fed into a separator 900 for the azeotropic distillation of the solution to remove the water. Operating temperature of separator 900 will depend on the azeotropic solvent used and the pressure maintained on the separator. The water may be removed from separator 900 through overhead line 912, optionally the aromatic compound recovered, and the remaining abated components may be fed via line 913 into contact zone 915 for contacting with the remaining catalyst components including the composition comprising the metal alkyl, the pyrrole-containing compound, the halide-containing compound (e.g., a metal halide or non-metal halide), the catalyst solvent, any remaining non-halide metal alkyl, metal alkyl halide, or combinations thereof, which may be placed into contact zone 915 via various input lines not shown in FIG. 3A. A catalyst product may then be withdrawn from contact zone 915 via line 970 and optionally filtered (not shown). Alternatively the water abated material comprising the chromium-containing compound may be stored prior to contact with the remaining catalyst components. Optionally, the abated components from line 913 may be subjected to further water abatement as described herein, for example contact with a non-halide metal alkyl, adsorbent, or both prior to contact with the remaining catalyst components.

In an embodiment, one or more catalyst components other than (i) a metal alkyl halide, (ii) a metal halide and a metal alkyl, or (iii) a non-metal halide and a metal alkyl, for example the composition comprising the chromium-containing compound, the composition comprising the pyrrole-containing compound, the non-metal halide-containing compound, the solvent, or combinations thereof are contacted with an adsorbent to abate water. The contacting may occur prior to contacting with (i) a metal alkyl halide, (ii) a metal halide and a metal alkyl, or (iii) a non-metal halide and a metal alkyl. In some embodiments, contacting the chromium-containing compound with the pyrrole-containing compound may enhance the solubility of the chromium-containing compound in a solvent (e.g. ethylbenzene) as well as reduce the solution viscosity. Thus, the reduced viscosity and more soluble solution may enhance the suitability of the solution to water abatement by means of passing it through an adsorbent such as molecular sieves, to remove all or a portion of any water present. In an embodiment, the pyrrole added may constitute substantially all or only a portion of the pyrrole required to make the catalyst composition. Other known means for reducing viscosity, enhancing solubility, or both may be employed such that a catalyst component becomes suitable for contact with an adsorbent to remove water.

Adsorption as used herein refers to the separation operation in which one component of a gas or liquid mixture is selectively retained in the pores of a resinous or microcrystalline solid. A gas or liquid mixture contacts a solid (the adsorbent) and a mixture component (the adsorbate, which is typically water) adheres to the surface of the solid. In an embodiment, an adsorbent may be used to abate water by adding the adsorbent to catalyst component(s) in a vessel and mixing thoroughly for adequate contacting of the adsorbent with the catalyst component(s). The mixture may then be allowed to stand and after a period of time, the adsorbent settles to the bottom of the vessel. Separation can be completed by decanting or filtration (e.g., suction filtration). Alternatively, water may be abated by passing the catalyst component(s) through a fixed adsorption bed comprised of an adsorbent, allowing the mixture adequate contact time for the adsorbate to sufficiently adhere to the adsorbent, and then removing the abated catalyst component(s) from the adsorption bed. The adsorbent may then be replaced or regenerated for the next use. The original adsorption capacity of the saturated bed may be recovered by any suitable regeneration method, for example, thermal regeneration, regeneration by pressure swing, or regeneration by purging.

In the embodiments, any suitable adsorbent may be used. Examples of suitable adsorbents include 3-Angstrom molecular sieves, 5-Angstrom molecular sieves, 13× molecular sieves, alumina, silica, or combinations thereof. 3-Angstrom (3 A) and 5-Angstrom (5 A) refers to the size of the molecule the material can adsorb, for example, the 3 A molecular sieve can adsorb molecules less than 3 angstrom and the 5 A molecular sieve can adsorb molecules less than 5 angstrom. Molecular sieves are crystalline structures not unlike sponges on a molecular scale. They have a solid framework defining large internal cavities where molecules can be adsorbed. These cavities are interconnected by pore openings through which molecules can pass. Because of their crystalline nature, the pores and cavities are the same size, and depending on the size of the openings, they can adsorb molecules readily, slowly, or not at all, thus functioning as molecular sieves—adsorbing molecules of certain sizes while rejecting larger ones.

Figure 3B:
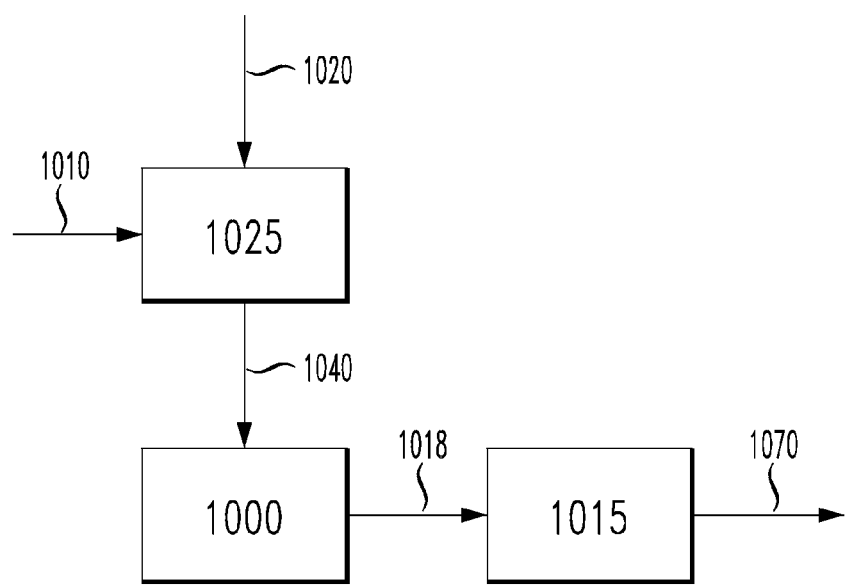

In an embodiment as illustrated in FIG. 3B, a pyrrole-chromium mixture may be formed in contact zone 1025 by contacting a composition comprising the pyrrole-containing compound fed to contact zone 1025 via line 1020 and the composition comprising the chromium-containing compound fed to contact zone 1025 via line 1010, which may occur about instantaneously or over a first period of time. Feeding of the chromium-containing composition and the pyrrole-containing composition to contact zone 1025 may be sequential (e.g. chromium followed by pyrrole or vice-versa) or simultaneous and at constant or varying Py:Cr ratios as disclosed previously. Once the pyrrole-chromium mixture has been contacted in contact zone 1025 the pyrrole-chromium mixture from contact zone 1025 may be passed to contact zone 1000 via line 1040. The pyrrole-chromium mixture may optionally contain solvent, other catalyst components, e.g. a non-metal halide, or combinations thereof, but does not comprise (i) a metal alkyl halide, (ii) a metal halide and a metal alkyl, or (iii) a non-metal halide and a metal alkyl. The pyrrole-chromium mixture is contacted with an adsorbent disposed in contact zone 1000. Contact zone 1000 may be a fixed adsorption bed as described in a previous embodiment, sized accordingly to the volumes of materials being adsorbed. The pyrrole-chromium mixture may be passed through the adsorption bed comprised of an adsorbent, e.g. 3 A molecular sieve, allowing for the adsorption process to occur over a second period of time to adsorb essentially all of the free water from the pyrrole-chromium mixture. Contact with the adsorbent in contact zone 1000 may be carried out according to various known methods.

The water abated mixture in contact zone 1000 may then be passed from contact zone 1000 via line 1018 and contacted with the remaining catalyst components in contact zone 1015 including the composition comprising the metal alkyl, a halide-containing compound (e.g., a metal halide or nonmetal halide), the solvent, any remaining non-halide metal alkyl, metal alkyl halide, or combinations thereof, which may be placed into contact zone 1015 via various input lines not shown in FIG. 3B. A catalyst product may then be withdrawn from contact zone 1015 via line 1070 and optionally filtered (not shown). Alternatively the water abated material comprising the chromium-containing compound may be stored prior to contact with the remaining catalyst components. Optionally, the water abated compounds from contact zone 1000 may be subjected to further water abatement as described herein, for example contact with a non-halide metal alkyl, azeotropic distillation, or both prior to contact with the remaining catalyst components.

Embodiments for abating water, acidic protons, or both as disclosed herein, for example the embodiments shown in FIGS. 2A-2D and 3A-3B, may be applied alone or in combination to other processes and catalyst compositions known in the art, for example, water, acidic protons, or both may be abated from the catalyst compositions or components disclosed in reference U.S. Pat. No. 6,133,495, U.S. App. No. 2002/0035029, WO 01/83447, WO 03/053890, and WO 03/053891, each of which is incorporated herein in its entirety. Likewise, embodiments for preparing catalysts, for example embodiments shown in FIGS. 1A-1D and 4A-4E, may be applied alone or in combination to other processes and catalyst compositions known in the art, for example those set forth in U.S. Pat. No. 6,133,495, 2002/0035029, WO 01/83447, WO 03/053890, and WO 03/053891. When applying the water abatement and catalyst preparation embodiments to these catalyst compositions or components disclosed in reference U.S. Pat. No. 6,133,495, U.S. App. No. 2002/0035029, WO 01/83447, WO 03/053890, and WO 03/053891, the appropriate substitutions and adjustment should be made for components that have a similar function; e.g. substitution of the multidentate ligands of WO 03/053890 and WO 03/053891 for the pyrrole compound used herein and adjustments of the ligand:Cr (pyrrole:chromium) molar ratios to account for the number of equivalents of ligand(s) per mole of the ligand. Furthermore, catalyst compositions or components disclosed in reference U.S. Pat. No. 6,133,495, U.S. App. No. 2002/0035029, WO 01/83447, WO 03/053890, and WO 03/053891 may be combined with other catalyst compositions or components as set forth herein to make various final catalysts according to various embodiments described herein, and water may be abated from any one or more of such compositions or components by any one or more abatement method disclosed herein.

In an embodiment, water, acidic protons, or both may be abated from the catalyst composition for producing an alpha-olefin oligomer disclosed in U.S. Pat. No. 6,133,495. A chromium-based catalyst is prepared by bringing a pyrrole ring-containing compound, an alkyl aluminum compound, and a halogen-containing compound into contact with each other in a hydrocarbon solvent, halogenated hydrocarbon solvent or mixture thereof, and then bringing the mixed resultant solution into contact with the chromium compound, wherein water, acidic protons, or both are abated from the catalyst or a component thereof prior to or during preparation of the catalyst. In an embodiment, the chromium-based catalyst is prepared by bringing the chromium compound, the pyrrole ring-containing compound, the alkyl aluminum compound, and the halogen-containing compound into contact with each other in a hydrocarbon solvent, halogenated hydrocarbon solvent or mixture thereof in the absence of alpha-olefin under such a condition that the concentration of the chromium compound in the resultant mixed solution is about $1\times10^{-7}$ to 1 mol/liter, alternatively about $1\times10^{-5}$ to $3\times10^{-2}$ mol/liter, alternatively adjusted to not more than about $8\times10^{-3}$ mol/liter, alternatively, not more than about 0.416 mg Cr/mL, wherein water, acidic protons, or both are abated from the catalyst or a component thereof prior to or during preparation of the catalyst. In an embodiment, water, acidic protons, or both are abated from a catalyst component comprising a pyrrole derivative represented by the general formula (I):

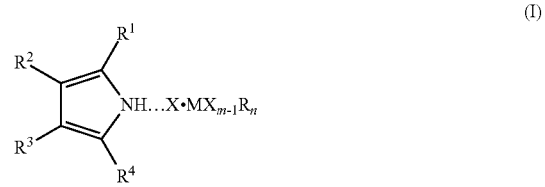

wherein $R^1$ to $R^4$ are a hydrogen atom or a linear or branched hydrocarbon group having 1 to 20 carbon atoms, in which $R^3$ and $R^4$ may integrally form a ring; X is a halogen atom; M is an element selected from the group consisting of those belonging to 3-Group, 4-Group, 6-Group (exclusive of chromium), 13-Group, 14-Group and 15-Group of the Periodic Table; m and n are numbers satisfying the relationships of $1 \leq m \leq 6$, $0 \leq n \leq 5$ and $2 \leq m+n \leq 6$ with the proviso that the sum of m and n is identical to the valence of the element M; n represents the number of Rs; and R is a hydrogen atom or a linear or branched hydrocarbon group having 1 to 20 carbon atoms and when n is not less than 2, and Rs may be the same or different.

In an embodiment, water, acidic protons, or both may be abated from the catalyst composition disclosed in US Patent No. 2002/0035029. In an embodiment, a catalyst for trimerization of ethylene comprises:

(i) an organometallic complex having a neutral multidentate ligand having a tripod structure, represented by the following formula (1):

wherein A may be a neutral multidentate ligand having a tripod structure, M may be a transition metal atom of group 3 to group 10 of the periodic table, each Q may be independently selected from the group consisting of a hydrogen atom, a halogen atom, a straight chain or branched alkyl group having 1 to 10 carbon atoms which may have a substituent, an aryl group having 6 to 10 carbon atoms which may have a substituent, and n is an integer equal to a formal oxidation valence of M, and (ii) an alkylaluminoxane;
said neutral multidentate ligand A in formula (1) being a tridentate ligand represented by the following formula (2) or formula (3):

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms which may have a substituent, or an aryl group having 6 to 10 carbon atoms which may have a substituent;

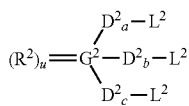  (3)

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element of group 14 or 17, $G^2$ represents a nitrogen or phosphorus atom when u is 0, or a phosphorus atom when u is 1, and $R^2$ represents an oxygen or sulfur atom. Water, acidic protons, or both may be abated from the catalyst or a component thereof prior to or during preparation of the catalyst.

In an embodiment, a catalyst for trimerization of ethylene comprises:

(i) an organometallic complex having a neutral multidentate ligand having a tripod structure, represented by the following formula (1):

AMQ$_n$  (1)

wherein A is a neutral multidentate ligand having a tripod structure, M is a transition metal atom of group 3 to group 10 of the periodic table, each Q is independently selected from the group consisting of a hydrogen atom, a halogen atom, a straight chain or branched alkyl group having 1 to 10 carbon atoms which may have a substituent, an aryl group having 6 to 10 carbon atoms which may have a substituent, and n is an integer equal to a formal oxidation valence of M, and (ii) an alkylaluminoxane, and
(iii) a halogenated inorganic compound;

said neutral multidentate ligand A in formula (1) being a tridentate ligand represented by the following formula (2) or formula (3):

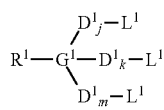  (2)

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms which may have a substituent, or an aryl group having 6 to 10 carbon atoms which may have a substituent;

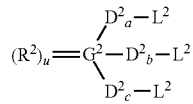  (3)

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element of group 14 or 17, $G^2$ represents a nitrogen or phosphorus atom when u is 0, or a phosphorus atom when u is 1, and $R^2$ represents an oxygen or sulfur atom. Water, acidic protons, or both may be abated from the catalyst or a component thereof prior to or during preparation of the catalyst.

In an embodiment, a catalyst for trimerization of ethylene comprises:

(i) an organometallic complex having a neutral multidentate ligand having a tripod structure, represented by the following formula (1):

AMQ$_n$  (1)

wherein A is a neutral multidentate ligand having a tripod structure, M is a transition metal atom of group 3 to group 10 of the periodic table, each Q is independently selected from the group consisting of a hydrogen atom, a halogen atom, a straight chain or branched alkyl group having 1 to 10 carbon atoms which may have a substituent, an aryl group having 6 to 10 carbon atoms which may have a substituent, and n is an integer equal to a formal oxidation valence of M, (ii) an alkylaluminoxane,
(iii) a halogenated inorganic compound, and
(iv) an alkyl group-containing compound represented by the following formula (4):

R$_p$EJ$_q$  (4)

wherein p and q are numbers satisfying the formulae: $0 \leq p \leq 3$ and $0 \leq q \leq 3$, provided that (P+q) is in the range of 1 to 3, E represents an atom, other than a hydrogen atom, of group 1, 2, 3, 11, 12 or 13 of the periodic table, each R independently represents an alkyl group having 1 to 10 carbon atoms, and each J independently represents a hydrogen atom, an alkoxide group having 1 to 10 carbon atoms, an aryloxy group having 6 to 10 carbon atoms, an aryl group having 6 to 10 carbon atoms or a halogen atom;

said neutral multidentate ligand A in formula (1) being a tridentate ligand represented by the following formula (2) or formula (3):

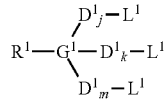  (2)

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms which may have a substituent, or an aryl group having 6 to 10 carbon atoms which may have a substituent;

(3)

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element of group 14 or 17, $G^2$ represents a nitrogen or phosphorus atom when u is 0, or a phosphorus atom when u is 1, and $R^2$ represents an oxygen or sulfur atom. Water, acidic protons, or both may be abated from the catalyst or a component thereof prior to or during preparation of the catalyst.

In an embodiment, a catalyst for trimerization of ethylene comprises:

(i) an organometallic complex having a neutral multidentate ligand having a tripod structure, represented by the following formula (1):

$$AMQ_n \quad (1)$$

wherein A is a neutral multidentate ligand having a tripod structure, M is a transition metal atom of group 3 to group 10 of the periodic table, each Q is independently selected from the group consisting of a hydrogen atom, a halogen atom, a straight chain or branched alkyl group having 1 to 10 carbon atoms which may have a substituent, an aryl group having 6 to 10 carbon atoms which may have a substituent, and n is an integer equal to a formal oxidation valence of M, (ii) an alkylaluminoxane, and (iii) an alkyl group-containing compound represented by the following formula (4):

$$R_pEJ_q \quad (4)$$

wherein p and q are numbers satisfying the formulae: $0 \leq p \leq 3$ and $0 \leq q \leq 3$, provided that (P+q) is in the range of 1 to 3, E represents an atom, other than a hydrogen atom, of group 1, 2, 3, 11, 12 or 13 of the periodic table, each R independently represents an alkyl group having 1 to 10 carbon atoms, and each J independently represents a hydrogen atom, an alkoxide group having 1 to 10 carbon atoms, an aryloxy group having 6 to 10 carbon atoms, an aryl group having 6 to 10 carbon atoms or a halogen atom;
said neutral multidentate ligand A in formula (1) being a tridentate ligand represented by the following formula (2) or formula (3):

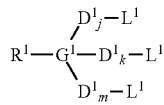
(2)

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms which may have a substituent, or an aryl group having 6 to 10 carbon atoms which may have a substituent;

(3)

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element of group 14 or 17, $G^2$ represents a nitrogen or phosphorus atom when u is 0, or a phosphorus atom when u is 1, and $R^2$ represents an oxygen or sulfur atom. Water, acidic protons, or both may be abated from the catalyst or a component thereof prior to or during preparation of the catalyst.

In an embodiment, a catalyst for trimerization of ethylene comprises:

(i) an organometallic complex having a neutral multidentate ligand having a tripod structure, represented by the following formula (1):

$$AMQ_n \quad (1)$$

wherein A is a neutral multidentate ligand having a tripod structure, M is a transition metal atom of group 3 to group 10 of the periodic table, each Q is independently selected from the group consisting of a hydrogen atom, a halogen atom, a straight chain or branched alkyl group having 1 to 10 carbon atoms which may have a substituent, an aryl group having 6 to 10 carbon atoms which may have a substituent, and n is an integer equal to a formal oxidation valence of M, (ii) an alkylaluminoxane, and (iii) at least one compound selected from the group consisting of an amine compound and an amide compound;
said neutral multidentate ligand A in formula (1) being a tridentate ligand represented by the following formula (2) or formula (3):

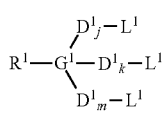
(2)

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three L¹s are not concurrently a substituent containing an element of group 14 or 17, G¹ represents a carbon or silicon atom, and R¹ represents a hydrogen atom, an alkyl group having 1 to 10 carbon atoms which may have a substituent, or an aryl group having 6 to 10 carbon atoms which may have a substituent;

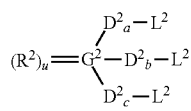  (3)

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element of group 14 or 17, $G^2$ represents a nitrogen or phosphorus atom when u is 0, or a phosphorus atom when u is 1, and $R^2$ represents an oxygen or sulfur atom. Water, acidic protons, or both may be abated from the catalyst or a component thereof prior to or during preparation of the catalyst.

In an embodiment, a catalyst for trimerization of ethylene comprises:

(i) an organometallic complex having a neutral multidentate ligand having a tripod structure, represented by the following formula (1):

$$AMQ_n \quad (1)$$

wherein A is a neutral multidentate ligand having a tripod structure, M is a transition metal atom of group 3 to group 10 of the periodic table, each Q is independently selected from the group consisting of a hydrogen atom, a halogen atom, a straight chain or branched alkyl group having 1 to 10 carbon atoms which may have a substituent, an aryl group having 6 to 10 carbon atoms which may have a substituent, and n is an integer equal to a formal oxidation valence of M, (ii) an alkylaluminoxane, (iii) at least one compound selected from the group consisting of an amine compound and an amide compound, and (iv) an alkyl group-containing compound represented by the following formula (4):

$$R_pEJ_q \quad (4)$$

wherein p and q are numbers satisfying the formulae: $0 \leq p \leq 3$ and $0 \leq q \leq 3$, provided that (P+q) is in the range of 1 to 3, E represents an atom, other than a hydrogen atom, of group 1, 2, 3, 11, 12 or 13 of the periodic table, each R independently represents an alkyl group having 1 to 10 carbon atoms, and each J independently represents a hydrogen atom, an alkoxide group having 1 to 10 carbon atoms, an aryloxy group having 6 to 10 carbon atoms, an aryl group having 6 to 10 carbon atoms or a halogen atom;

said neutral multidentate ligand A in formula (1) being a tridentate ligand represented by the following formula (2) or formula (3):

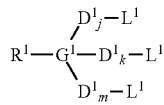  (2)

wherein j, k and m independently represent an integer of 0 to 6, each $D^1$ independently represents a divalent hydrocarbon group which may have a substituent, each $L^1$ independently represents a substituent containing an element of group 14, 15, 16 or 17 of the periodic table, with the proviso that all of the three $L^1$s are not concurrently a substituent containing an element of group 14 or 17, $G^1$ represents a carbon or silicon atom, and $R^1$ represents a hydrogen atom, an alkyl group having 1 to 10 carbon atoms which may have a substituent, or an aryl group having 6 to 10 carbon atoms which may have a substituent;

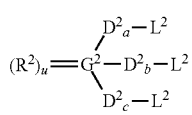  (3)

wherein a, b and c independently represent an integer of 0 to 6; u represents an integer of 0 or 1; each $D^2$ independently represents a divalent hydrocarbon group which may have a substituent; each $L^2$ independently represents a substituent containing an element of group 14, 15, 16 or 17 of the periodic table, with the proviso that all of the three $L^2$s are not concurrently a substituent containing an element of group 14 or 17, $G^2$ represents a nitrogen or phosphorus atom when u is 0, or a phosphorus atom when u is 1, and $R^2$ represents an oxygen or sulfur atom. Water, acidic protons, or both may be abated from the catalyst or a component thereof prior to or during preparation of the catalyst.

In an embodiment, an olefin oligomerization catalyst system incorporates a halogen source into a pyrrole ligand as disclosed in WO 01/83447, and water, acidic protons, or both may be abated from the catalyst system or a component thereof prior to or during preparation of the catalyst. In an embodiment, water, acidic protons, or both are abated from a catalyst component comprising a halopyrrole ligand. The catalyst system may comprise a chromium source, a metal alkyl, and the halopyrrole ligand and may be utilized for producing 1-hexene by trimerizing ethylene.

In an embodiment, an olefin oligomerization catalyst system incorporates a mixed heteroatomic ligand with at least three heteroatoms, of which at least one heteroatom is sulfur and at least 2 heteroatoms are not the same, as disclosed in WO 03/053890, and water, acidic protons, or both may be abated from the catalyst system or a component thereof prior to or during preparation of the catalyst. In an embodiment, water, acidic protons, or both are abated from the catalyst system or a catalyst component comprising a multidentate mixed heteroatomic ligand, which includes at least three heteroatoms of which at least one is a sulfur atom. The catalyst system may comprise a chromium source, a metal alkyl, an aluminoxane, and the multidentate mixed heteroatomic ligand and may be utilized for producing 1-hexene by trimerizing ethylene.

In an embodiment, water, acidic protons, or both may be abated from the ligand and the ligand may be comprised of the following ligand types:

(a) $R^1A(R^2BR^3)(R^4CR^5)$ wherein $R^1$, $R^3$ and $R^5$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^2$ and $R^4$ may be the same or different and are $C_1$ to about $C_{15}$ hydrocarbyls; A is nitrogen or phosphorous; and B and C are sulfur; and (b) $R^1A(R^2BR^3R^4)(R^5CR^6)$ wherein $R^1$, $R3^1$, $R^4$, and $R^6$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^2$ and $R^5$ may be the same or different and are $C_1$ to about $C_{15}$ hydrocarbyls; A and B are individually nitrogen or phosphorous; and C is sulfur; and (c) $A(R^1BR^2R^3)(R^4CR^5)$ wherein $R^2$, $R^3$, and $R^5$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^1$ and $R^4$ may be the same or different and are $C_1$ to about $C_{15}$ hydrocarbyls; B is nitrogen or phosphorous; and A and C are sulfur; and (d) $A(R^1BR^2R^3)(R^4CR^5R^6)$ wherein $R^2$, $R^3$, $R^5$, and $R^6$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^1$ and $R^4$ may be the same or different and are $C_1$ to about $C_{15}$ hydrocarbyls; B and C are individually nitrogen or phosphorous; and A is sulfur.

In an embodiment the ligand may comprise bis(2-ethylsulfanyl-ethyl)-amine, bis-(2-methylsulfanyl-ethyl)-amine, bis-(2butylsulfanyl-ethyl)-amine, bis-(2-decylsulfanyl-ethyl)-amine, bis-(2butylsulfanyl-ethyl)-amine, bis-(2-decylsulfanyl-ethyl)-amine, bis-(ethylsulfanylmethyl)-amine, bis-(2-ethylsulfanyl-phenyl)-amine, bis-(2-ethylsulfanyl-ethyl)phosphine, bis-(2-ethylsulfanyl-ethyl)-ethylphosphine, bis-(2-ethylsulfanylethyl)-phenylphosphine, N-methylbis-(2-ethylsulfanyl-ethyl)-amine, (2-ethylsulfanyl-ethyl)(3-ethylsulfanyl-propyl)-amine, (2-ethylsulfanyl-ethyl)(2diethylphosphino-ethyl)-amine, (2-ethylsulfanyl-ethyl)(2-diethylphosphinoethyl)-sulfide, (2-ethylsulfanyl-ethyl)(2-diethylamino-ethyl)-amine and (ethylsulfanyl-ethyl)(2-diethylamino-ethyl)-sulfide, (2-ethylsulfanyl-ethyl)(2diethylphosphino-ethyl)-phosphine, (2-ethylsulfanyl-ethyl)(2-diethylaminoethyl)-ethylphosphine, bis-(2-diethylphosphino-ethyl)-sulfide, bis-(2diethylamino-ethyl)-sulfide, (2-diethylphosphino-ethyl)(2-diethylamino-ethyl)sulfide and derivatives thereof, wherein water, acidic protons, or both may be abated from the ligand.

In an embodiment, an olefin oligomerization catalyst system incorporates a mixed heteroatomic ligand with at least three heteroatoms, of which at least heteroatom is nitrogen and at least two heteroatoms are not the same, as disclosed in WO 03/053891, and water, acidic protons, or both may be abated from the catalyst system or a component thereof prior to or during preparation of the catalyst. In an embodiment, the ligand may be a multidentate mixed heteroatomic ligand for an oligomerization of olefins catalyst, which ligand includes at least three heteroatoms. At least one heteroatom may be nitrogen and at least two heteroatoms may not be the same. The ligand may contain, in addition to nitrogen, at least one phosphorous heteroatom. In an embodiment, the ligand may be selected such that none of the non-carbon based heteroatoms are directly bonded to any of the other non-carbon based heteroatoms. In an embodiment, the ligand may not include a sulfur heteroatom. In an embodiment, water, acidic protons, or both may be abated from a ligand having the structure $R^1A(R^2BR^3R^4)(R^5CR^6R^7)$ wherein $R^1$, $R^3$, $R^4$, $R^6$ and $R^7$ may be hydrogen or independently be selected from the groups consisting of alkyl, aryl, aryloxy, halogen, nitro, alkoxycarbonyl, carbonyloxy, alkoxy, aminocarbonyl, carbonylamino, dialkylamino, or derivatives thereof, or aryl substituted with any of these substituents; $R^2$ and $R^5$ are the same or different and are $C_1$ to about $C_{1-5}$ hydrocarbyls; and at least A, B or C is nitrogen with the remainder of A, B and C being individually nitrogen or phosphorous.

In an embodiment the ligand may comprise bis-(2-diethylphosphino-ethyl)-amine, bis-(diethylphosphino-methyl)-amine, bis-(2-diethylphosphino-phenyl)-amine, N-methyl-bis-(2-diethylphosphino-ethyl)-amine, bis-(2-diphenylphosphino-ethyl)-amine, (2-diethylphosphino-ethyl)(3-diethylphosphino-propyl)-amine, bis-(2-dicyclohexylphosphino-ethyl)-amine, N-benzylbis-(2-diethylphosphino-ethyl)-amine, N-methyl-(2-diethylphosphino-ethyl)(3-diethylphosphino-propyl)-amine, (2-diethylphosphinoethyl)(2-diethylamino-ethyl)-amine, N-methyl-(2-diethylphosphino-ethyl)(2-diethylaminoethyl)-amine and bis-(2-diethylamino-ethyl)ethylphosphine. A suitable multidentate mixed heteroatomic ligand is bis-(2-diethylphosphino-ethyl)-amine and derivatives thereof, wherein water, acidic protons, or both may be abated from the ligand.

In an embodiment, a nitrogen-containing compound may be contacted with the metal alkyl prior to contacting the metal alkyl with the chromium-containing compound, the pyrrole-containing compound, the halide-containing compound, the solvent, or combinations thereof, to make a catalyst for use in oligomerizing an olefin. Typically, preparation of catalyst can result in undesirable reaction products of metal alkyls, e.g., aluminum alkyls, with water impurities. Water present in the catalyst components at the time they are added to the metal alkyl compound may be a source of precipitates that can lead to polymer formation in the oligomerization reaction. Such precipitates may be abated by the addition of a nitrogen compound to the metal alkyl, thereby enhancing the solubility of the undesirable reaction products and preventing them from precipitating out, and further minimizing polymer production in the oligomerization reaction.

The nitrogen-compound may be comprised of amines, pyrroles, pyridines, substituted pyrroles such as indoles, di and tri nitrogen heterocycles, or combinations thereof. In an embodiment, the nitrogen-compound may be 2,5-dimethylpyrrole, which in this case the nitrogen compound can serve in two different functions: one, in the formation of the active site in the catalyst system; and two, in preventing the precipitation of the product of the water and metal alkyl reaction (as a solubility enhancer). In an embodiment, the nitrogen-containing compound is tributyl amine. In an embodiment, the final catalyst product is comprised of from about 0.01 to about 10 moles nitrogen per mole metal; alternatively the final catalyst product is comprised of from about 0.05 to about 5 moles nitrogen to mole metal; or alternatively the final catalyst product is comprised of from about 0.1 to about 0.5 moles nitrogen to mole metal.

In an embodiment for making a catalyst comprising a chromium-containing compound, a pyrrole-containing compound, a metal alkyl, a halide-containing compound, and optionally a solvent for use in oligomerizing an olefin, the chromium-containing compound, the pyrrole-containing compound, and the metal alkyl may be simultaneously contacted. In an embodiment the simultaneous contact of the catalyst components occur via addition to a single contact zone. The simultaneous contacting may occur over a period of time of from about 1 minute to about 12 hours; alternatively from about 1 minute to about 6 hours; or alternatively from about 1 minute to about 3 hours. In an embodiment, the simultaneous contacting may occur over a period of less than or equal to about 120 minutes to form a catalyst product. In an embodiment, one or more of the catalyst components may be fed to the contact zone at mass flow rates of from about 0.1 Kg/hr to about 500 Kgs/hr, alternatively from about 5 Kg/hr to about 250 Kgs/hr; alternatively from about 10 Kg/hr to about 150 Kgs/hr; alternatively from about 0.1 Kg/hr to about 100 Kgs/hr; alternatively from about 0.1 Kg/hr to 50 Kgs/hr; alternatively from about 0.5 Kg/hr to 25 Kgs/hr; or alternatively from about 1.0 Kg/hr to 10 Kgs/hr. Such mass flow rates may also be employed with other embodiments described herein. In an embodiment, the simultaneous contacting is performed in a continuous process (wherein the period of time may be an extended period of time), or alternatively in a batch process. In an embodiment, the metal alkyl may be in a solution comprising a non-metal halide and a metal alkyl, a metal alkyl halide, a metal halide and a metal alkyl, or combinations thereof. In an embodiment, the halide-containing compound may also be simultaneously contacted with the chromium-containing compound, the pyrrole-containing compound, and the metal alkyl, for example by simultaneous addition to the hydrocarbon solvent.

Figure 4A:
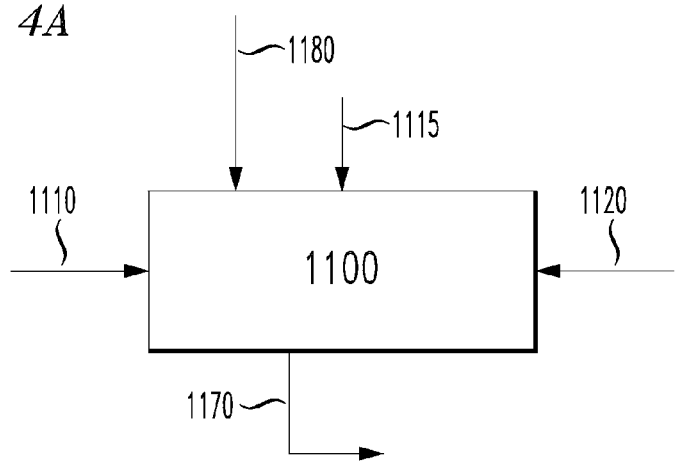
FIGS. 4A through 4E illustrate various embodiments of a method of preparing an oligomerization catalyst comprising simultaneous addition of catalyst components.
Figure 4B:
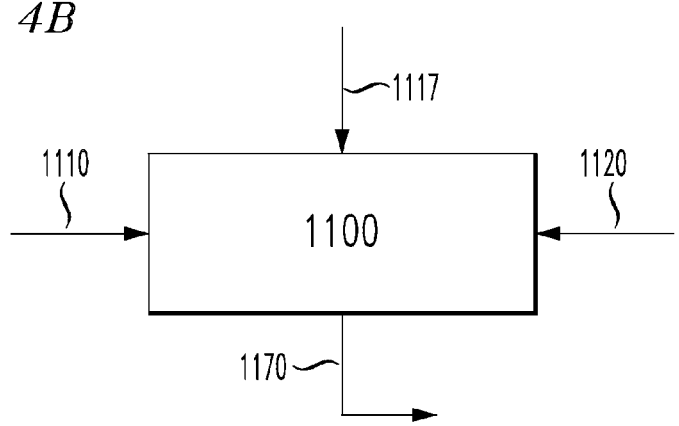
Figure 4C:
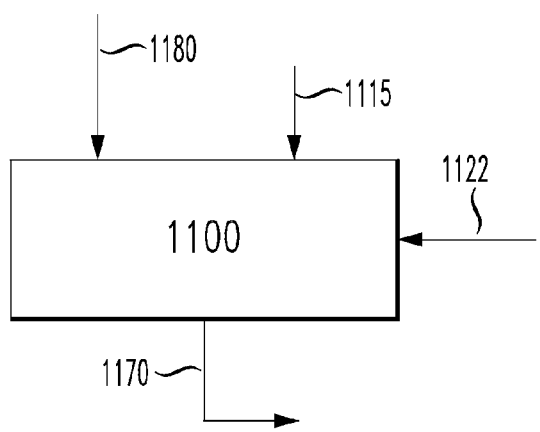
Figure 4D:
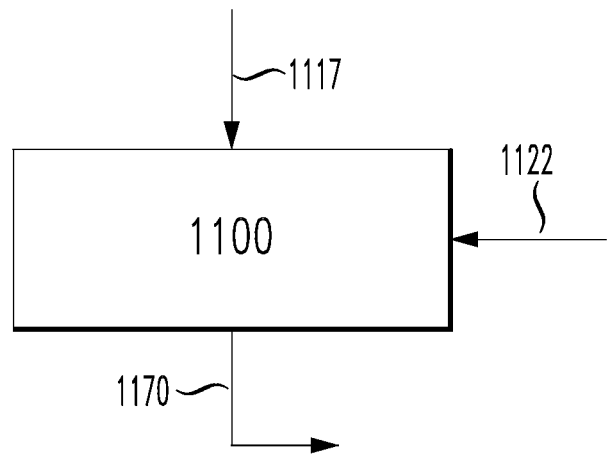

In an embodiment as shown in FIG. 4A, the composition comprising the chromium-containing compound may be fed into contact zone 1100 via line 1110, the composition comprising the pyrrole-containing compound may be fed into contact zone 1100 via line 1120, the composition comprising the metal alkyl may be fed into contact zone 1100 via line 1115, and the composition comprising the halide-containing compound may be fed into contact zone 1100 via line 1180, all compositions being fed into contact zone 1100 simultaneously over a period of time. In an embodiment as shown in FIG. 4B, the composition comprising the chromium-containing compound may be fed into contact zone 1100 via line 1110, the composition comprising the pyrrole-containing compound may be fed into contact zone 1100 via line 1120, the compositions comprising the metal alkyl and the halide-containing compound may be pre-contacted and fed into contact zone 1100 via line 1117, the final compositions being fed into contact zone 1100 simultaneously over a period of time. In an embodiment as shown in FIG. 4C, the compositions comprising the chromium-containing compound and the pyrrole-containing compound may be pre-contacted and fed into contact zone 1100 via line 1122, the composition comprising the metal alkyl may be fed into contact zone 1100 via line 1115, and the compositions comprising the halide-containing compound may be fed into contact zone 1100 via line 1180, the final compositions being fed into contact zone 1100 simultaneously over a period of time. In an embodiment as shown in FIG. 4D, the compositions comprising the chromium-containing compound and the pyrrole-containing compound may be pre-contacted and fed into contact zone 1100 via line 1122 and the compositions comprising the metal alkyl and the halide-containing compound may be pre-contacted and fed into contact zone 1100 via line 1117, the final compositions being fed into contact zone 1100 simultaneously over a period of time. In the embodiments shown in FIGS. 4A-4D, a hydrocarbon solvent may be placed in contact zone 1100 before, after, or concurrently with addition of the various catalyst components. Contact zone 1100 may comprise a single vessel, for example a storage tank, tote, container, mixing vessel, etc. A catalyst product may be withdrawn from contact zone 1100 via line 1170 and optionally filtered (filter not shown). In the embodiments shown in FIGS. 4A-4D, the addition of the composition comprising the pyrrole-containing compound and the composition comprising the chromium-containing compound may be made in constant or varying Py:Cr ratios as disclosed previously. Additionally, the water, acidic protons, or both abatement embodiments set forth in FIGS. 2A-2D and 3A-3B may be combined with the simultaneous addition embodiments of FIGS. 4A-4D.

In an embodiment for making a catalyst comprising a chromium-containing compound, a pyrrole-containing compound, a metal alkyl, a halide-containing compound, and optionally a solvent for use in oligomerizing an olefin, the compositions comprising the chromium-containing compound, the pyrrole-containing compound, the metal alkyl, optionally the halide-containing compound, or combinations thereof may be contacted with a previously prepared oligomerization catalyst composition. The previously prepared oligomerization catalyst solution may comprise the same or different chromium-containing compound, pyrrole-containing compound, metal alkyl, and halide-containing compound. The halide-containing compound may comprise a metal halide, a metal alkyl halide, or combinations thereof.

Any of the embodiments disclosed herein for making catalysts may be carried out wherein the new catalyst may be prepared in one or more contact zones comprising existing, previously prepared active catalyst. For example, in the embodiments shown in FIGS. 4A-D, contact zone 1100 may be a holding tank for active catalyst to be fed to an oligomerization reactor and be comprised of previously prepared oligomerization catalyst. The various catalyst compounds in lines 1110, 1115, 1117, 1120, 1122, and 1180 may be simultaneously combined with the previously prepared oligomerization catalyst composition in contact zone 1100.

Figure 4E:
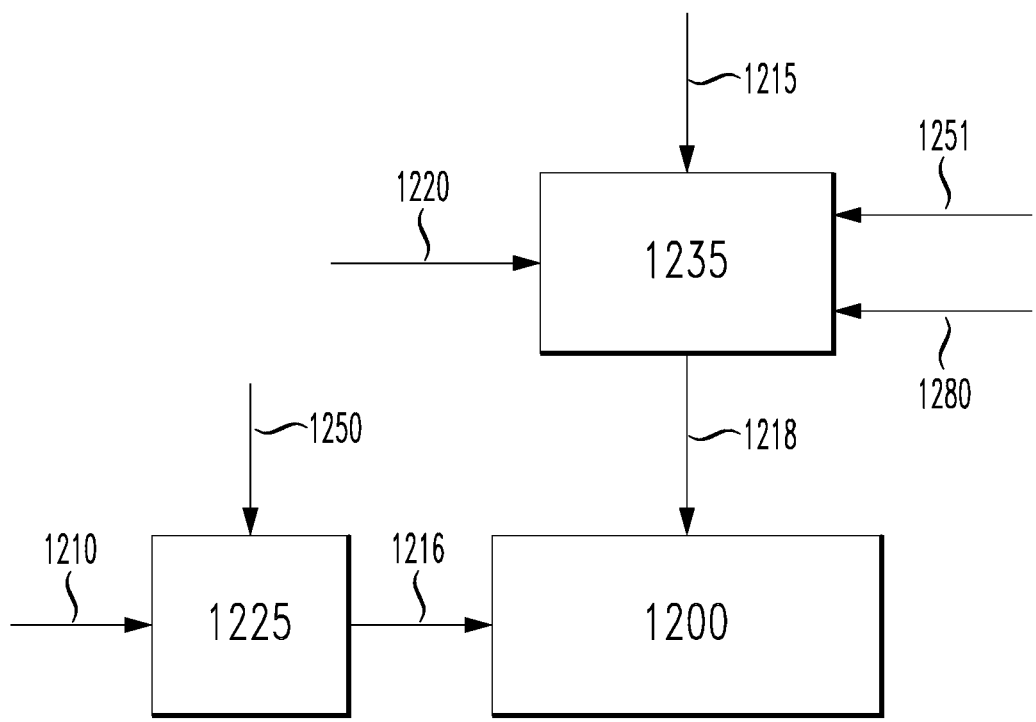

In an embodiment as shown in FIG. 4E, contact zone 1200 may be a holding tank for active catalyst to be fed to an oligomerization reactor and comprises previously made oligomerization catalyst. The chromium-containing compound in line 1210 may be combined with a hydrocarbon solvent in line 1250 forming a first solution in contact zone 1225. The pyrrole-containing compound in line 1220, the metal alkyl in line 1215, and the optional halide-containing compound in line 1280 may be combined with the hydrocarbon solvent in line 1251 forming a second solution in contact zone 1235. The hydrocarbon solvent in line 1250 may be the same or different hydrocarbon solvent in line 1251. The first solution in contact zone 1225 and the second solution in contact zone 1235 may then be contacted (e.g., simultaneously or sequentially, including a plurality of iterative addition sequences) with the previously made oligomerization catalyst composition in contact zone 1200 via lines 1216 and 1218, respectively, to make the new catalyst composition. Optionally, a mixer may be disposed in contact zone 1200 to thoroughly mix the new and existing catalyst components. Again, the contacting of the composition comprising the pyrrole-containing compound and the composition comprising the chromium-containing compound may be made in constant or varying Py:Cr ratios as disclosed previously. Additionally, the water, acidic protons, or both abatement embodiments set forth in FIGS. 2A-2D and 3A-3B may be combined with the simultaneous addition embodiment of FIG. 4E.

Contacting of the catalyst components can be done under any conditions sufficient to thoroughly contact the components. Typically, contacting is performed in an inert atmosphere, such as, for example, nitrogen and/or argon. The reaction temperature for the disclosed methods of making a catalyst for use in oligomerizing an olefin can be any temperature. For ease of operation, ambient temperature may be employed. In order to effectuate a more efficient reaction, temperatures which maintain the reaction mixture in a liquid state are desirable. In an embodiment, reaction temperature is maintained at less than about 120° C.; alternatively less than about 100° C.; alternatively less than about 75° C.; alternatively less than about 50° C.; or alternatively less than about 25° C. when contacting the compositions comprising the chromium-containing compound, the pyrrole-containing compound, the metal alkyl, the halide-containing compound, or combinations thereof to make the catalyst. The preparation of the catalyst system at a low temperature may increase catalyst activity and reduce levels of undesirable co-product polymer.

The reaction pressure for the disclosed methods of making a catalyst for use in oligomerizing an olefin can be any pressure which does not adversely effect the reaction. Generally, pressures within the range of from about atmospheric pressure to about three atmospheres are acceptable. For ease of operation atmospheric pressure may be employed.

The reaction time for the disclosed methods of making a catalyst for use in oligomerizing an olefin can be any amount of time that can react substantially all reactants (i.e., catalyst components). Depending on the reactants, as well as the reaction temperature and pressure, reaction time can vary. Usually, times of less than about 1 day can be sufficient, for example from about 1 minute to about 12 hours. In an embodiment, reaction time is from about 1 minute to about 6 hours, alternatively from about 1 minute to about 3 hours. Longer times usually provide no additional benefit and shorter times may not allow sufficient time for complete reaction.

The resultant olefin oligomerization catalyst system prepared as described above in any of the embodiments can be collected and kept under a dry, inert atmosphere to maintain chemical stability and reactivity. In an embodiment, it may be desirable to contact the catalyst with the olefin within about 1000 hours of preparation of the catalyst; alternatively the catalyst may be contacted with the olefin within about 800 hours of preparation of the catalyst; alternatively the catalyst may be contacted with the olefin within about 600 hours of preparation of the catalyst; alternatively the catalyst may be contacted with the olefin within about 400 hours of preparation of the catalyst; or alternatively the catalyst may be contacted with the olefin within about 200 hours of preparation of the catalyst. In an embodiment, the olefin oligomerization catalyst comprising the chromium-containing compound, the pyrrole-containing compound, the metal alkyl, the halide-containing compound, and optionally the solvent may product a product (e.g., hexane) having a purity of at least 99.4 at a time within about 200 hours after preparation of the catalyst; alternatively the product may have a purity of at least about 99.3 at a time within about 400 hours after preparation of the catalyst; alternatively the product may have a purity of at least about 99.1 at a time within about 600 hours after preparation of the catalyst; alternatively the product may have a purity of at least about 98.8 at a time within about 800 hours after preparation of the catalyst; or alternatively the product may have a purity of less than about 98.8 at a time greater than about 900 hours after preparation catalyst.

The chromium-containing compound may be one or more organic or inorganic chromium compounds, with a chromium oxidation state of from about 0 to about 6. As used in this disclosure, chromium metal may be included in this definition of a chromium compound. Generally, the chromium-containing compound will have a formula of $CrX_n$, wherein X can be the same or different and can be any organic or inorganic radical, and n may be an integer from 0 to 6. Suitable organic radicals can have from about 1 to about 20 carbon atoms per radical, and are selected from alkyl, alkoxy, ester, ketone, amino radicals, or combinations thereof. The organic radicals can be straight-chained or branched, cyclic or acyclic, aromatic or aliphatic, and can be made of mixed aliphatic, aromatic, and/or cycloaliphatic groups. Suitable inorganic radicals include, but are not limited to halides, sulfates, oxides, or combinations thereof.

The chromium-containing compound may be a chromium (II) compound, chromium (III) compound, or combinations thereof. Suitable chromium (III) compounds include, but are not limited to, chromium carboxylates, chromium naphthenates, chromium halides, chromium pyrrolides, chromium benzoates, chromium dionates, or combinations thereof. Specific chromium (III) compounds include, but are not limited to, chromium (III) isooctanoate, chromium (III) 2,2,6,6-tetramethylheptanedionate, chromium (III) naphthenate, chromium (III) chloride, chromium (III) tris(2-ethylhexanoate), chromic bromide, chromic chloride, chromic fluoride, chromium (III) oxy-2-ethylhexanoate, chromium (III) dichloroethylhexanoate, chromium (III) acetylacetonate, chromium (III) acetate, chromium (III) butyrate, chromium (III) neopentanoate, chromium (III) laurate, chromium (III) stearate, chromium (III) oxalate, chromium (III) benzoate, chromium (III) pyrrolide(s), or combinations thereof. Suitable chromium (II) compounds include, but are not limited to, chromous fluoride, chromous chloride, chromous bromide, chromous iodide, chromium (II) bis(2-ethylhexanoate), chromium (II) acetate, chromium (II) butyrate, chromium (II) neopentanoate, chromium (II) laurate, chromium (II) stearate, chromium (II) oxalate, chromium (II) benzoate, chromium (II) pyrrolide(s), or combinations thereof. In an embodiment, the chromium-containing compound may be chromium (III) 2-ethylhexanoate.

In an embodiment, the monomeric chromium content and the residual (excess) radicals are optimized. This value is designated by the ratio moles Cr:((moles ligand x number of coordination equivalents of the ligand/mole of ligand)/Cr oxidation number). In an embodiment the ratio moles Cr:((moles ligand x number of coordination equivalents of the ligand/mole of ligand)/Cr oxidation number) is from about 0.9:1 to about 1.1:1, alternatively from about 0.94:1 to about 1.08:1, alternatively from about 0.97:1 to about 1.05:1.

In an embodiment the chromium compound is chromium (III) 2-ethylhexanoate. The weight percent chromium is in the range from about 10.3 wt % to 12.8 wt %; alternatively from 10.4 wt % to 11.8 wt %; alternatively from 10.5 wt % to 11.2 wt %. The amount of chromium oligomers is low such that the chromium compound demonstrates methanol solubility. The amount of free acid is below 50 weight percent; alternatively below 30 weight percent; alternatively below 20 weight percent. Particulates, insoluble in hexane, are below 1 weight percent; alternatively below 0.5 weight percent; alternatively below 0.2 weight percent. Water content is below 1 weight percent; alternatively below 0.5 weight percent; alternatively below 0.2 weight percent.

The pyrrole-containing compound can be any pyrrole-containing compound that will react with a chromium salt to form a chromium pyrrolide complex. The pyrrole-containing compound includes hydrogen pyrrolide, e.g., pyrrole ($C_4H_5N$), derivatives of pyrrole, as well as metal pyrrolide complexes, alkali metal pyrrolides, salts of alkali metal pyrrolides, or combinations thereof. A pyrrolide (or a pyrrole) can be any compound comprising a 5-membered, nitrogen-containing heterocycle, such as pyrrole, derivatives of pyrrole, substituted pyrrole, and mixtures thereof. Broadly, the pyrrole-containing compound can be pyrrole, any heteroleptic or homoleptic metal complex or salt containing a pyrrolide radical or ligand, or combinations thereof.

Generally, the pyrrole-containing compound will have from about 4 to about 20 carbon atoms per molecule. Pyrrolides (or pyrroles) include hydrogen pyrrolide (pyrrole), derivatives of pyrrole, substituted pyrrolides (or pyrroles), lithium pyrrolide, sodium pyrrolide, potassium pyrrolide, cesium pyrrolide, the salts of substituted pyrrolides, or combinations thereof. Examples of substituted pyrrolides (or pyrroles) include, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-propionate, ethyl-3,5-dimethyl-2-pyrrole-carboxylate In an embodiment the pyrrole containing compound is 2,5-dimethylpyrrole. The content of 2,5-dimethylpyrrole is greater than 98 weight percent; alternatively greater than 99.0 weight percent; alternatively greater than 99.5 weight percent. The water content of the pyrrole containing compound is below 1 weight percent; alternatively below 0.5 weight percent; alternatively below 0.01 weight percent. The color of the pyrrole containing compound (Platinum-Cobalt Number) is below 200; alternatively below 120; alternatively below 80.

In an embodiment, the pyrrole-containing compound used in an oligomerization catalyst system comprises a dimeric pyrrole compound, for example one or more compounds represented by the following general structures:

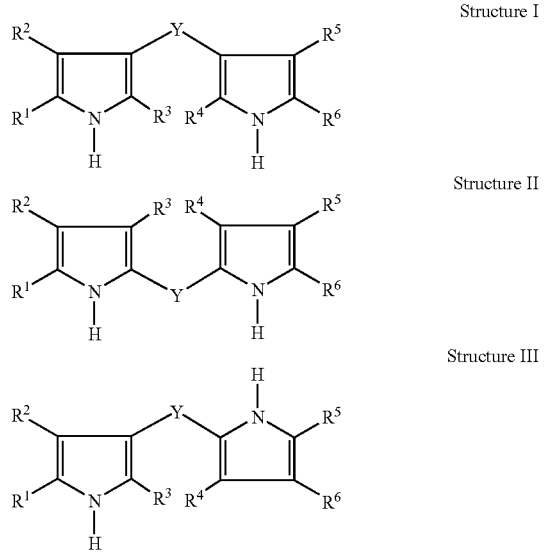

Structure I

Structure II

Structure III wherein, each $R^1$-$R^6$ may independently be H, or a $C_1$-$C_{20}$ aromatic group, or any two vicinal to each other, taken together with the carbon atom to which they are bonded may form an aromatic or non-aromatic ring. Y is a structural bridge having 1 to 20 carbon atoms and may include linear, branched, or cyclic paraffinic or aromatic or contain cyclic paraffinic or aromatic structures and may include hetero atoms such as oxygen or sulfur in the form of linear, branched, or cyclic ether, silyl, sulfide, sulfone, sulfoxide functionality.

In an embodiment shown as Structure (I), $R^1$, $R^3$, $R^4$, and $R^6$ are methyl group, $R^2$ and $R^5$ are hydrogens, and Y=$(CH_2)_n$ wherein n=1-10. In an embodiment shown as Structure (II), $R^1$ and $R^6$ are methyl groups, $R^2$-$R^5$ are hydrogens, and Y=$(CH_2)_n$ wherein n=1-10. In an embodiment shown as Structure (III), $R^1$, $R^3$, and $R^5$ are methyl groups, $R^2$, $R^4$, and $R^6$ are hydrogen, and Y=$(CH_2)_n$ wherein n=~1-10.

Use of the dimeric pyrroles may produce a catalyst system with activity and selectivity to a desired oligomerized product, such as, for example, the trimerization of ethylene to 1-hexene, as well as low polymer production.

The metal alkyl, sometimes referred to as an activating compound, may be a heteroleptic or homoleptic metal alkyl compound of any of the metals aluminum, boron, lithium, magnesium, or zinc. The metal alkyl may be a metal alkyl halide such as DEAC; a non-halide metal alkyl such as TEA; or combinations thereof. One or more metal alkyls can be used. The ligand(s) on the metal can be aliphatic, aromatic, or combinations thereof. For example, the ligand(s) may be any saturated or unsaturated aliphatic radical. The metal alkyl may be a compound that can be considered both a Lewis acid and a metal alkyl. As used in this disclosure, a Lewis acid may be defined as any compound that may be an electron acceptor. Activating compounds which are both a metal alkyl and a Lewis acid include alkylaluminum compounds, alkylmagnesium, alkylzinc, alkyllithium compounds, or combinations thereof. The metal alkyl can have any number of carbon atoms. However, due to commercial availability and ease of use, the metal alkyl will usually comprise less than about 70 carbon atoms per metal alkyl molecule and alternatively less than about 20 carbon atoms per molecule. In an embodiment, the metal alkyls are non-hydrolyzed, i.e., not pre-contacted with water, such as alkylaluminum compounds, derivatives of alkylaluminum compounds, halogenated alkylaluminum compounds, and mixtures thereof for improved product selectivity, as well as improved catalyst system reactivity, activity, productivity, or combinations thereof. In an embodiment the metal alkyl may be non-halide metal alkyl, a metal alkyl halide, a non-hydrolyzed alkylaluminum compound, a hydrolyzed alkylalumimum compound, or combinations thereof.

Suitable non-halide metal alkyls include, but are not limited to, alkylaluminum compounds, alkyl boron compounds, alklymagnesium compounds, alkylzinc compounds, alkyllithium compounds, or combinations thereof. Suitable non-halide metal alkyls include, but are not limited to, n-butyllithium, s-butyllithium, t-butyllithium, diethylmagnesium, dibutylmagnesium, diethylzinc, triethylaluminum, trimethylaluminum, tripropylaluminum, tributylaluminum, triisobutylaluminum, tri-n-hexylaluminum, tri-n-octylaluminum, diethylaluminum ethoxide, diethylaluminum phenoxide, and mixtures thereof. Suitable metal alkyl halide compounds include, but are not limited to, ethylaluminum dichloride, diethylaluminum chloride, diethylaluminum bromide, diethylaluminum sesquichloride, diisobutylaluminum chloride, ethylaluminum sesquichloride, diethylaluminum bromide, diethylaluminum iodide, ethylaluminumethoxychloride, and mixtures thereof. In an embodiment, the alkylaluminum compound may be triethylaluminum.

When a trimerization catalyst system may be the desired product, the metal alkyl may be at least one non-hydrolyzed alkylaluminum compound, expressed by the general formulae $AlR_3$, $AlR_2X$, $AlRX_2$, $AlR_2OR$, $AlRXOR$, $Al_2R_3X_3$, or combinations thereof, wherein R may be an alkyl group and X may be a halogen atom. Suitable compounds include, but are not limited to, trimethylaluminum, triethylaluminum, tripropylaluminum, tri-n-butylaluminum, tri-iso-butylaluminum, tri-n-hexylaluminum, tri-n-octylaluminum, diethylaluminumchloride, diethylaluminumbromide, diethylaluminumethoxide, diethylaluminum phenoxide, ethylaluminumethoxychloride, ethylaluminum dichloride, diethylaluminum chloride, diethylaluminum bromide, ethylaluminum sesquichloride, or combinations thereof. In an embodiment, the activating compound for an oligomerization catalyst system may be a trialkylaluminum compound, $AlR_3$, for example triethylaluminum. Additionally, hydrolyzed alkylaluminum compounds, aluminoxanes, may be used. Aluminoxanes can be prepared as known in the art by reacting water or water containing materials with trialkylaluminium compounds. Suitable aluminoxanes are prepared from trialkylaluminium compounds such as trimethylaluminium, triethylaluminium, tripropylaluminium, tributylaluminium, trisobutylaluminium, trihexylaluminium or the like, and mixtures thereof. Mixtures of different aluminoxanes may also be used. Suitable hydrolyzed alkylaluminum compounds include, but are not limited to methylaluminoxane, modified methylaluminoxane, and ethylaluminoxanes, and mixtures thereof.

The olefin oligomerization catalyst systems can further comprise a catalyst support. A supported chromium catalyst system can be prepared with any support useful to support a chromium catalyst. Suitable catalyst supports include, but are not limited to, zeolites, inorganic oxides, either alone or in combination, phosphated inorganic oxides, and mixtures thereof, for example silica, silica-alumina, alumina, fluorided alumina, silated alumina, thoria, aluminophosphate, aluminum phosphate, phosphated silica, phosphated alumina, silica-titania, coprecipitated silica/titania, fluorided/silated alumina, and mixtures thereof. In an embodiment, the catalyst support, is aluminophosphate.

The solvent may be a hydrocarbon solvent, a halogenated hydrocarbon solvent, or combinations thereof, usually having not more than 30 carbon atoms. Specific examples of the solvents may include aliphatic and alicyclic saturated hydrocarbons such as isobutane, pentane, n-hexane, hexanes, cyclohexane, n-heptane or n-octane, aliphatic and alicyclic unsaturated hydrocarbons such as 2-hexene, cyclohexene or cyclo-octene, aromatic hydrocarbons such as toluene, benzene or xylenes, othro-xylene, meta-xylene, paraxylene, chlorobenzene, halogenated hydrocarbons such as carbon tetrachloride, chloroform, methylene chloride or chlorobenzene or dichlorobenzene, or the like. In an embodiment, the hydrocarbon solvent may be an aromatic or a halogenated aromatic compound having between about 6 to about 20 carbon atoms; a saturated or unsaturated hydrocarbon having from about 3 to about 14 carbon atoms; a halogenated saturated hydrocarbon having from about 1 to about 9 carbon atoms; or combinations thereof. The solvent may be a hydrocarbon such as cyclohexane, isobutane, n-hexane, hexanes, n-heptane, heptanes, pentane, or mixtures thereof. In an embodiment the solvent is ethylbenzene. In an embodiment the solvent is tetradecene. In an embodiment, alpha-olefins may be used as the solvent, for example 1-hexene. In an embodiment, the solvent may comprise normal and/or isomeric mixtures of butene, hexene, octene, decene, dodecene, tetradecene, or combinations thereof.

In an embodiment, the hydrocarbon compound used as a solvent can be any combination of one or more aromatic or aliphatic unsaturated hydrocarbon compounds. While not wishing to be bound by theory, it may be believed that an unsaturated hydrocarbon compound acts as more than a solvent, and can be a reactant, a stabilizing component, or both, either during, subsequent, or both, to formation of an inventive catalyst system. Suitable unsaturated hydrocarbon compounds can be any unsaturated hydrocarbon compound that can solubilize the catalyst system. In an embodiment, aromatic compounds having from about 6 to about 20 carbon atoms per molecule as a solvent there can be used in combination with any unsaturated aliphatic hydrocarbon comprising less than about 20 carbon atoms per molecule. Specific unsaturated aliphatic compounds include ethylene, 1-hexene, 1,3-butadiene, and mixtures thereof. In an embodiment, the unsaturated aliphatic hydrocarbon compound may be ethylene, which may be both a solvent and a reactant. Specific unsaturated aromatic hydrocarbon compounds include, but are not limited to, toluene, benzene, ortho-xylene, metaxylene, para-xylene, ethylbenzene, xylene, mesitylene, hexamethylbenzene, and mixtures thereof.

The halide-containing compound can be any compound containing a halogen, for example organohalides (including those listed as suitable solvents); non-organohalides; metal halides (including metal alkyl halides such as those previously described and non-alkyl metal halides such as tin tetrachloride and magnesium chloride); non-metal halides; or combinations thereof. Suitable compounds include, but are not limited to, compounds with a general formula of $R_mX_n$, wherein R can be any organic radical, inorganic radical, or both, X can be a halide, selected from fluoride, chloride, bromide, iodide, or combinations thereof, and m and n each are numbers greater than 0. Where R is an organic radical, R may have from about 1 to about 70 carbon atoms per radical, alternatively from 1 to 20 carbon atoms per radical, for best compatibility and catalyst system activity. Where R is an inorganic radical, R may be selected from aluminum, silicon, germanium, hydrogen, boron, lithium, tin, gallium, indium, lead, and mixtures thereof. In an embodiment, the halide-containing compound is a chloride-containing compound such as DEAC or organochlorides. Specific organo halides compounds include, but are not limited to, methylene chloride, chloroform, benzylchloride chlorobenzene, carbon tetrachloride, chloroethane, 1,1-dichloroethane, 1,2-dichloroethane, tetrachloroethane, hexachloroethane, 1,4-dibromobutane, 1-bromobutane, aryl chloride, carbon tetrabromide, bromoform, bromobenzene, iodomethane, diiodomethane, hexafluorobenzene trichloro-acetone, hexachloro-acetone, hexachloro-cyclohexane, 1,3,5-trichloro-benzene, hexachloro-benzene, trityl chloride, or mixtures thereof. Specific non-alkyl metal halides include but are not limited to silicon tetrachloride, tin (II) chloride, tin (IV) chloride, germanium tetrachloride, boron trichloride, scandium chloride, yttrium chloride, lanthanum chloride, titanium tetrachloride, zirconium tetrachloride, hafnium tetrachloride, aluminum chloride, gallium chloride, silicon tetrachloride, tin tetrachloride, phosphorus trichloride, antimony trichloride, trityl-hexachloro-antimonate, antimony pentachloride, bismuth trichloride, boron tribromide, silicon tetrabromide, aluminum fluoride, molybdenum pentachloride, tungsten hexachloride, aluminum tribromide, aluminum trichloride, or combinations thereof. Specific metal alkyl halide compounds include, diethyl aluminum chloride, ethyl aluminum sesquichloride, ethyl aluminum dichloride, mixture of non-halide metal alkyls and metal halides, trimethylchlorosilane, tributyl tin chloride, dibutyl tin dichloride, or combinations thereof.

Furthermore, the chromium-containing compound, the metal alkyl, or solvent can contain and provide a halide to the reaction mixture. For example, the halide source may be an alkylaluminum halide and may be used in conjunction with alkylaluminum compounds. Suitable alkylaluminum halides include, but are not limited to, diisobutylaluminum chloride, diethylaluminum chloride, ethylaluminum sesquichloride, ethylaluminum dichloride, diethylaluminum bromide, diethylaluminum iodide, and mixtures thereof.

The amount of each reactant used to prepare an oligomerization catalyst system can be any amount sufficient that, when combined to form the catalyst system, oligomerization occurs upon contact with one or more olefins. Generally, a molar excess of the metal alkyl is used. In an embodiment, expressed as a molar ratio, in terms of moles of nitrogen (N) in the pyrrole compound to moles of metal (M) in the metal alkyl, usually at least a 1:150 molar ratio is used. In an embodiment, the metal (M) is aluminum. In an embodiment, the N:M molar ratio is from about 1:1 to about 1:50, alternatively from about 1:1 to about 1:20, or alternatively from about 1:1 to about 1:10. Generally, the amount of metal alkyl/pyrrole solution used is determined based on the moles of chromium. In an embodiment, expressed as a molar ratio, in terms of moles of chromium (Cr) to moles of nitrogen (N) in the pyrrole compound to moles of metal (M) in the metal alkyl, i.e., Cr:N:M, the ratio of the chromium containing compound to the pyrrole-containing compound is at least about 1:15 and the ratio of the chromium containing compound to metal alkyl is at least about 1:150 such that Cr:N:M is at least about 1:15:150. In an embodiment, the Cr:N:M molar ratio is within a range of about 3:3:3 (also expressed as about 1:1:1) to about 1:3:100; alternatively, the Cr:N:M molar ratio is within a range of 1:3:9 to 1:3:21. In an embodiment, to prepare an oligomerization catalyst system, about one mole of chromium, as the element chromium (Cr), can be contacted with about 1 to about 50 moles of pyrrole-containing compound and about 1 to about 75 moles of aluminum, as the element, optionally in an excess of unsaturated hydrocarbon. The halide source may be present in an amount from about 1 to about 75 moles of halide, as the element. In an embodiment, about 1 mole of chromium, calculated as the element chromium (Cr), can be contacted with about 1 to about 15 moles of pyrrole-containing compound; about 5 to about 40 moles of aluminum, calculated as the element aluminum (Al); and about 1 to about 30 moles of the halide-containing compound, calculated as elemental halide (X); in an excess of unsaturated hydrocarbon. In an embodiment, about one mole of chromium, as the element (Cr), may be contacted with two to four moles of pyrrole-containing compound; 10 to 2 moles of aluminum, as the element (Al); and 2 to 15 moles of halide, as an element (X); in an excess of unsaturated hydrocarbon.

The ratio of pyrrole to chromium (Py:Cr) in the final catalyst composition recovered as product from the various embodiments disclosed herein is referred to as the final Py:Cr molar ratio. The final Py:Cr molar ratio of the catalyst may be in a range of from about 1.0:1 to about 4.0:1; alternatively from about 1.5:1 to about 3.7:1; alternatively from about 1.5:1 to about 2.5:1; alternatively from about 2.0:1 to about 3.7:1; alternatively from about 2.5:1 to about 3.5:1; or alternatively from about 2.9:1 to about 3.1:1.

The catalyst synthesis prepared in a hydrocarbon solvent may be referred to as a catalyst system solution. The resultant catalyst system, prior to introduction to any of the reactant, may have a chromium concentration of about less than about 50 mg Cr/ml catalyst system solution, for example from about 0.005 g Cr/mL catalyst system solution to about 25 mg Cr/ml catalyst system solution, alternatively from about 0.1 mg Cr/ml catalyst system solution to about 25 mg Cr/ml catalyst system solution, alternatively from about 0.5 mg Cr/ml catalyst system solution to about 15 mg Cr/ml catalyst system solution, or alternatively from about 1 mg Cr/ml catalyst system solution to about 15 mg Cr/ml catalyst system solution Catalysts prepared in accordance with the present disclosure may be used for the oligomerization of olefins, for example, alpha-olefins. The oligomerization of olefins may be conducted by any suitable oligomerization methods. In an embodiment, an oligomerization catalyst is contacted with one or more olefins in a reaction zone under suitable reaction conditions (e.g., temperature, pressure, etc.) to oligomerize the olefins. Linear or branched alpha-olefins having 2 to 30 carbon atoms can be used as the olefins raw material. Specific examples of the alpha-olefins may include ethylene, propylene, 1-butene, 1-hexene, 1-octene, 3-methyl-1-butene, 4-methyl-1-pentene or the like. When ethylene is used as the alpha-olefin, it is possible to produce 1-hexene as a trimer of ethylene with a high yield and a high selectivity.

In the description above, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present disclosure is susceptible to embodiments of different forms. There are shown in the drawings, and herein are described in detail, specific embodiments of the present disclosure with the understanding that the present disclosure is to be considered an exemplification of the principles of the invention, and is not intended to limit the invention to that illustrated and described herein. It is to be fully recognized that the different teachings of the embodiments discussed above may be employed separately or in any suitable combination to produce desired results. Specifically, the present disclosure for a method of making a catalyst by contacting of catalyst components should not be limited by any of the various embodiments described. Various embodiments set forth in the figures may be combined. For example, the water, acidic protons, or both abatement embodiments set forth in FIGS. 2A-2D and 3A-3B may be combined with the bulk addition embodiments of FIGS. 1A-1D or the simultaneous addition embodiments of FIGS. 4A-4E. Additionally, various embodiments for abating water may be combined in any desired number and sequence, for example azeotropic distillation followed by contact with a non-halide metal alkyl (e.g., TEA), contact with an adsorbent, or both in any order; contact with a non-metal halide followed by contact with an adsorbent (or vice-versa); azeotropic distillation before, after, or between contact with a non-metal halide followed by contact with an adsorbent; etc. The water, acidic protons, or both abatement, bulk addition, and simultaneous addition embodiments may be integrated in any desired and operable number and sequence in other embodiments. The method disclosed herein is for making an oligomerization catalyst that may be useful in any suitable reaction such that the reaction is an oligomerization reaction. In an embodiment, the method of the present disclosure is for a trimerization catalyst for use in a trimerization reaction producing 1-hexene from ethylene and the detailed description above may be focused on this embodiment but with the understanding that the present invention may have broader applications.

EXAMPLES

Preparation of an Oligomerization Catalyst Having been Generally Described, the following examples are given as particular embodiments of the catalyst disclosed and to demonstrate the practice and advantages thereof. It is understood that the examples are given by way of illustration and are not intended to limit the specification or the claims to follow in any manner.

Various embodiments for preparing the oligomerization catalyst are shown in examples 1 through 14. In example 1, selective 1-hexene catalyst is prepared at various temperatures and chromium concentrations. In example 2, selective 1-hexene catalyst is prepared by simultaneous addition of chromium/ethylbenzene and TEA/DEAC/pyrrole/ethylbenzene to the heel of previously prepared catalyst. In example 3, selective 1-hexene catalyst is prepared by using a pyrrole:

chromium ratio of 6:1 for the first half of the chromium/pyrrole addition and a pyrrole:chromium ratio of 0 during the second half of the chromium/pyrrole addition. In example 4, selective 1-hexene catalyst is prepared by simultaneous addition of all catalyst components. In example 5, chromium compounds containing various amounts of water and chromium oligomers are used in the preparation of the selective 1-hexene catalyst. In example 6, selective 1-hexene catalyst is prepared by separate but simultaneous addition of the pyrrole and chromium components to a solution of TEA and DEAC. In example 7, selective 1-hexene catalyst is improved when a small amount of TEA is added to the chromium component and water, acidic protons, or both are abated. In example 8, water, acidic protons, or both are abated in the preparation of the selective 1-hexene catalyst by contacting a small amount of TEA with the chromium/pyrrole solution. In example 9, preparation of the selective 1-hexene catalyst is made by varying the pyrrole:chromium ratio during the addition to TEA/DEAC.

In example 10, preparation of the selective 1-hexene catalyst is made using high initial pyrrole:chromium contact ratios when contacted with TEA/DEAC. In example 11, preparation of the selective 1-hexene catalyst is made using simultaneous separate addition of catalyst components to the heel of previously prepared catalyst. In example 12, preparation of the selective 1-hexene catalyst is made with the addition of a nitrogen compound to the alkylaluminum compound to solubilize products resulting from the reaction of water and aluminum alkyls. In example 13, water is abated when the pyrrole and chromium components are contacted to reduce the chromium component's viscosity, facilitating water removal using molecular sieves. In example 14, water is abated by azeotropic distillation to remove the water from the chromium catalyst component. In example 15, the impact of the catalyst age on 1-hexene purity is described. Several of the above examples also include the embodiment for the addition of chromium and/or pyrrole to the alkyl aluminums.

In the examples below, catalyst was prepared using one of two apparatus set-ups. One set-up is a lab scale set-up for preparing catalyst in small quantities, for example 100 ml, which are typically used for screening purposes. The other set-up is a pilot plant scale set-up typically designed for preparing larger quantities of catalyst, for example 3.5 gallons, which would be suitable for use in a pilot plant.

The lab scale set-up prepares catalyst in a dry box in which the atmosphere inside the box is controlled with a helium blanket keeping it free of oxygen and moisture, which may be detrimental to the catalyst components, the prepared catalysts, or both. All lab scale catalyst preparation procedures described in the examples below are performed in glassware in a dry box. Once the catalyst is prepared it is diluted with cyclohexane to the concentration desired for oligomerization reactor tests. The diluted catalyst solution is then transferred into a 300 cc metal cylinder to provide the means for transport of the catalyst to an oligomerization reactor under protected atmosphere. Note that any transfer of components via syringes described in the examples below is done in the dry box.

The pilot plant scale set-up prepares catalyst under a nitrogen blanket to control the atmosphere, keeping it free of oxygen and moisture. All pilot plant scale catalyst preparation procedures described in the examples below are performed in a 5 gallon reactor comprising a hasteloy steel autoclave. Once the catalyst is prepared it is filtered into a 5-10 gallon metal cylinder. About 150 grams of the prepared catalyst is then transferred from the large cylinder into a smaller, 300 cc, metal cylinder and transported to a helium blanketed dry box as described above. The prepared catalyst is transferred into glassware and is diluted with cyclohexane to the desired concentration for testing in the oligomerization reactor. The diluted catalyst solution is then transferred into a 300 cc metal cylinder and transported to an oligomerization reactor.

In the examples below, the prepared catalyst is tested in either a batch or a continuous oligomerization reactor. The batch oligomerization reactor is a 1 liter autoclave that is sealed and is under a nitrogen blanket. It has a magnetic stirring device to stir the contents of the sealed container. Prepared catalyst solution transported to the oligomerization reactor in the 75 cc metal cylinder. Solvent, e.g., cyclohexane, is charged to the oligomerization reactor, and the catalyst is transferred to the reactor by connecting the cylinder to the reactor and pressurizing the cylinder with ethylene, which conveys the catalyst into the reactor. The oligomerization reactor is pressurized with 650 psig of ethylene and 50 psig of hydrogen, and is operated at a temperature of about 115° C.

In some of the examples below, a continuous oligomerization reactor is used to test the prepared catalyst. The continuous oligomerization is preformed by controlling of all the feeds to the reactor by using separate controls for each feed component. Hydrogen is fed to the reactor at a rate of about 0.5 L/hr, and ethylene is fed to the reactor at a rate of about 497 g/hr. The reactor is either a 1 liter or a 1 gallon autoclave, depending on the desired residence time in the reactor. Reaction temperature is about 115° C., and pressure is about 800 psig.

Online samples of production from the continuous oligomerization reactor were collected via liquid sampling valves (manufactured by Valco) and fed to an online gas chromatograph (GC), a Hewlett Packard 6890, for analysis. The productions samples were analyzed by the GC for the amount of ethylene present, hexene present, and $C_6$ isomers and higher oligomers present. From this information the selectivity, purity, and conversion was calculated. Selectivity (1-$C_6$=) refers to the weight percent of ethylene converted into 1-hexene. Purity (1-$C_6$=/$C_6$) refers to the weight percent of 1-hexene in the total of all $C_6$ isomers. Conversion ($C_2$=) refers to the weight percent of ethylene has been converted to oligomer product (e.g., hexene or decenes, etc.). Productivity refers how much 1-hexene the catalyst produced, and relates to the amount of catalyst is used. Productivity is quantified in units of grams of 1-hexene per gram of chromium (g 1-$C_6$=/g Cr). In the batch processes, productivity is evaluated over a 30 minute time frame. Other evaluations made on the oligomerization processed catalyst examples include reactor polymer (Rx Polymer) and total polymer. At the end of each day, the reactor was opened and cleaned. Any formed polymer inside the reactor was collected, allowed to dry, and then weighed. This amount was then scaled up to a commercial sized processing unit of 100,000,000 pounds/year and reported as reactor polymer, quantified in pounds per hour expected in a 100,000,000 pound per year plant (Lb/Hr 100 MM/yr Plant). A filter comprising a stainless steel pad placed downstream of the reactor was also removed, dried and weighed at the end of each day for amounts of polymer. This amount of polymer was then scaled up to a 100,000,000 pounds/year plant and added to the reactor polymer amount for reporting the total polymer, quantified in pounds per hour expected in a 100,000,000 pound per year plant (Lb/Hr 100 MM/yr Plant).

To determine the presence of water of hydration in some of the samples an infrared analysis was done using a standard IR apparatus. The IR band for the complexed water, e.g., about 1450 $cm^{-1}$, of hydration is near the band for chromium oligomers, making it difficult to distinguish the two. Therefore, in some cases a methanol solution test for precipitation of chromium oligomers was performed to help in evaluating the online samples to determine the presence of water of hydration.

Example 1

Catalyst 1-8: Catalyst was prepared by adding 14.1 lbs of dry, nitrogen-purged toluene to a 5 gallon reactor. To the toluene was added 630.9 g chromium (III) 2-ethylhexanoate dissolved in 750 mL toluene followed by a 300 mL toluene rinse. 2,5-Dimethylpyrrole (388.9 mL) was added to the chromium solution in the reactor. The reactor was purged with nitrogen and brought to a temperature of 25° C. A mixture of 1,600 g neat triethylaluminum (TEA) and 1,229 g neat diethylaluminum chloride (DEAC) was then added to the reactor followed by 0.2 lbs of toluene rinse. The temperature increased 18° C. and was returned to 25° C. with cooling. The contents of the reactor stood overnight and were then filtered, using a filter comprising a combination of a metal screen, filter paper, glass wool, diatomaceous earth, and another layer of glass wool. Additional catalysts were prepared in which the temperature and chromium concentration of the catalyst preparations were varied. The catalysts were tested for productivity in a 1 gallon continuous reactor and the results are shown in Table 1.

TABLE 1

| Catalyst | Temp (° C.) | Concentration (mg Cr/mL) | Productivity (g 1-C6=/g Cr) | Rx Polymer (Lb/Hr 100 MM/yr Plant) |
|---|---|---|---|---|
| Ratio Cr/pyrrole/TEA/DEAC (1/3/11/8) | | | | |
| 1 | 25 | 1 | 43,183 | 0.001 |
| 2 | 75 | 1 | 40,010 | 0.083 |
| 3 | 25 | 5 | 45,769 | 0.005 |
| 4 | 75 | 5 | 44,599 | 0.000 |
| Ratio Cr/pyrrole/TEA/DEAC (1/1.8/6.5/5) | | | | |
| 5 | 25 | 1 | 41,961 | 0.015 |
| 6 | 75 | 1 | 38,008 | 0.005 |
| 7 | 25 | 5 | 43,373 | 0.016 |
| 8 | 75 | 5 | 27,127 | 0.906 |

The examples show that catalyst productivity increased with a reduction in catalyst preparation temperature. Additionally, the examples show the best catalyst productivity was observed in catalyst 3 and catalyst 7 with 45,769 g 1-C6=/g Cr and 43,373 g 1-C6=/g Cr, respectively, when prepared at low temperature (25° C.) and high chromium concentration (5 mg Cr/mL). Low reactor polymer was also observed under the best productivity conditions.

Example 2

Catalyst 9-10: An ethylbenzene solution containing 2.3 g chromium (III) 2-ethylhexanoate and 8.13 g ethylbenzene was prepared. A separate solution containing 6.05 g neat triethylaluminum (TEA), 4.63 g neat diethylaluminum chloride (DEAC), 1.37 g 2,5-dimethylpyrrole and 22.6 g ethylbenzene was also prepared. These two solutions were added to 30.98 g of active catalyst over a 40 minute period such that the addition time for both solutions started and ended at the same time. The catalyst was tested in a 1 L continuous reactor and the average results of two test runs are shown in Table 2 as Catalyst 10. The average of two test runs of a standard catalyst preparation is shown in Table 2 as Catalyst 9.

TABLE 2

| Catalyst | Selectivity (1-$C_6$=) | Purity (1-$C_6$=) | Productivity (g 1-$C_6$=/g Cr) | Rx Polymer (Lb/Hr 100 MM/yr Plant) | Total Polymer |
|---|---|---|---|---|---|
| 9 | 89.3% | 98.8% | 82,575 | 0.00 | 13.33 |
| 10 | 89.1% | 98.7% | 82,989 | 0.00 | 7.18 |

The examples show that an acceptable catalyst can be prepared. The examples further indicate that a fewer number of tanks may be required to prepare catalyst.

Example 3

Catalyst 11: A solution was prepared by mixing 12.10 g neat triethylaluminum (TEA), 9.38 g neat diethylaluminum chloride (DEAC) and 20.02 g ethylbenzene. Two aliquots were added to this solution. The first contained 2.3 g chromium (III) 2-ethylhexanoate, 1.14 g ethylbenzene and 2.74 g 2,5-dimethylpyrrole. The second contained 2.3 g chromium (III) 2-ethylhexanoate and 1.14 g ethylbenzene. Ethylbenzene was added to obtain a total volume of 100 mL. The catalyst prepared by this method was tested in a 1 L continuous reactor. The average results of three test runs are shown in Table 3.

TABLE 3

| Catalyst | Selectivity (1-$C_6$=) | Purity (1-$C_6$=/$C_6$) | Catalyst Productivity (g 1-$C_6$=/g Cr) |
|---|---|---|---|
| 11 | 91.2% | 99.2% | 80,759 |

The example shows high selectivity (91.2%), high purity (99.2%), and good catalyst productivity (80,759 g 1-$C_6$=/g Cr) for the catalyst preparation.

Example 4

Catalyst 12: Ethylbenzene (10.67 g) was added to a dry 100 mL volumetric flask. Individual chemicals were added to each of four separate 20 mL syringes. The chemicals added were 4.76 g chromium (III) 2-ethylhexanoate dissolved in 2.38 g ethylbenzene, 12.06 g neat triethylaluminum (TEA), 9.26 g neat diethylaluminum chloride (DEAC) and 2.74 g 2,5-dimethylpyrrole. To each of these syringes was added sufficient ethylbenzene to provide a total volume of 19-20 mL. The needles of the syringes were added to the 100 mL volumetric flask and the syringes emptied into the flask simultaneously at the same rate over 30 minutes. After the additions were complete, ethylbenzene was added to the flask to obtain a total volume of 100 mL. The catalyst (1 mL) prepared by this method was tested in a 1 L batch reactor at 116° C. and 680 psig. The results of this test are shown in Table 4.

TABLE 4

| Catalyst | Selectivity (1-$C_6$=) | Purity (1-$C_6$=/$C_6$) | Catalyst Productivity (g 1-$C_6$=/g Cr) |
|---|---|---|---|
| 12 | 92.0% | 98.7% | 34,325 |

Example 5

Catalyst 13-15: Catalyst was prepared by adding 15.85 g ethylbenzene to a dry 100 mL volumetric flask. To this flask was added 12.09 g neat triethylaluminum (TEA), 9.26 g neat diethylaluminum chloride (DEAC) and 2.74 g 2,5-dimethylpyrrole. To this mixture was added 4.76 g chromium (III) 2-ethylhexanoate dissolved in 2.38 g ethylbenzene. The volume was brought to 100 mL with ethylbenzene. Different preparations of chromium (III) 2-ethylhexanoate were used to prepare the catalysts 13-15. In catalyst 13 the chromium content of the chromium (III) 2-ethylhexanoate was 10.5%. Infrared analysis and a methanol solubility test indicated that some water of hydration was present but no chromium oligomers. In catalyst 14 the chromium content was 10.9% and infrared analysis and methanol solubility indicated that neither water of hydration nor chromium oligomers were present. In catalyst 15 the analysis indicated the presence of chromium oligomers. The catalysts prepared were tested for activity in the continuous reactor (1 L) and the average results for two test runs of each preparation are shown in Table 5.

TABLE 5

| Catalyst | Selectivity ($1-C_6$=) | Purity ($1-C_6$=/$C_6$) | Conversion ($C_2$=) | Catalyst Productivity (g $1-C_6$=/g Cr) |
|---|---|---|---|---|
| 13 | 90.3% | 99.1% | 79.0% | 83,642 |
| 14 | 88.7% | 99.1% | 84.5% | 87,882 |
| 15 | 87.4% | 98.1% | 86.4% | 88,460 |

The examples show that the best combination of purity and productivity are obtained when the water of hydration and chromium oligomers are not contained in the chromium (III) 2-ethylhexanoate in significant amounts.

Example 6

Catalyst 16: Ethylbenzene (20.01 g) was added to a dry 125 mL Erlenmeyer flask equipped with a magnetic stirrer. To the ethylbenzene was added 12.07 g neat triethylaluminum and 9.27 g neat diethylaluminum chloride. Into a 10 mL syringe was added 4.61 g chromium (III) 2-ethylhexanoate dissolved in 2.28 g ethylbenzene. Into a separate 10 mL syringe was added 2.73 g 2,5-dimethylpyrrole and 3.38 g ethylbenzene. Both of the syringes had an approximate volume of 7.5 mL. The syringe needles were put into opposite sides of the Erlenmeyer flask containing the diluted aluminum alkyls and the contents were added simultaneously over 30 minutes. After the addition was complete, the contents were transferred to a 100 mL volumetric flask and diluted to about 103 mL with ethylbenzene. This catalyst was tested in a continuous 1 L reactor and the results (average of three test runs) are shown in Table 6.

TABLE 6

| Catalyst | Selectivity ($1-C_6$=) | Purity ($1-C_6$=/$C_6$) | Conversion ($C_2$=) | Catalyst Productivity (g $1-C_6$=/g Cr) |
|---|---|---|---|---|
| 16 | 93.0% | 98.9% | 66.6% | 72,691 |

Example 7

Catalyst 17: Neat triethylaluminum (TEA, 0.27 g) was added to 30.01 g of ethylbenzene. This solution was added slowly to 4.62 g chromium (III) 2-ethylhexanoate dissolved in 2.27 g ethylbenzene. This is an amount of TEA sufficient to react with water and excess acid present in the chromium (III) 2-ethylhexanoate. The chromium solution, after reaction with TEA, was added, over 50 minutes, to a solution containing TEA (11.81 g), diethylaluminum chloride (DEAC, 9.27 g), 2,5-dimethylpyrrole (2.75 g) and ethylbenzene (25.01 g). Ethylbenzene was subsequently added to provide a total volume of 100 mL.

Catalyst 18: A comparison catalyst was prepared by adding 30.02 g of ethylbenzene to 4.62 g chromium (III) 2-ethylhexanoate dissolved in 2.27 g ethylbenzene. The chromium solution was added, over 50 minutes, to a solution containing TEA (12.08 g), diethylaluminum chloride (DEAC, 9.28 g), 2,5-dimethylpyrrole (2.74 g) and ethylbenzene (25.00 g). Ethylbenzene was subsequently added to provide a total volume of 100 mL.

These catalysts were tested for productivity in a 1 L continuous reactor. The average of two separate runs for each catalyst is shown in Table 7.

TABLE 7

| Catalyst | Selectivity ($1-C_6$=) | Purity ($1-C_6$=/$C_6$) | Conversion ($C_2$=) | Catalyst Productivity (g $1-C_6$=/g Cr) |
|---|---|---|---|---|
| 17 | 90.0% | 98.8% | 88.3% | 93,129 |
| 18 | 89.1% | 98.8% | 82.7% | 86,306 |

The addition of TEA to a chromium (III) 2-ethylhexanoate solution provided a catalyst with increased activity. It will also reduce corrosion in equipment after the catalyst has been inactivated. The example further provides an example of TEA addition to chromium to abate water, acidic protons, or both.

Example 8

Catalyst 19: Neat triethylaluminum (TEA, 0.43 g) was added to 2.01 g of ethylbenzene. This solution was added slowly to 4.62 g chromium (III) 2-ethylhexanoate in 27.27 g ethylbenzene. This is a small excess of the amount of TEA sufficient to react with water and excess acid present in the chromium (III) 2-ethylhexanoate. To this chromium/TEA solution was added 2.73 g of 2,5-dimethylpyrrole. The chromium/TEA/dimethylpyrrole solution, was added, over 30-40 minutes, to a solution containing TEA (11.62 g), diethylaluminum chloride (DEAC, 9.25 g) and ethylbenzene (15.00 g). Ethylbenzene was then added to provide a total volume of 100 mL.

Catalyst 20: A comparison catalyst was prepared by adding 2.74 g 2,5-dimethylpyrrole to 4.61 g chromium (III) 2-ethylhexanoate dissolved in 2.27 g ethylbenzene. An immediate reduction in the viscosity of the chromium solution was observed. This chromium solution was added, over 30-40 minutes, to a solution containing TEA (12.08 g), diethylaluminum chloride (DEAC, 9.27 g) and ethylbenzene (20.00 g). Ethylbenzene was then added to provide a total volume of 100 mL.

These catalyst preparations were tested for productivity in a 1 L continuous reactor. The average of three separate test runs for each catalyst is shown in Table 8.

TABLE 8

| Catalyst | Selectivity ($1-C_6$=) | Purity ($1-C_6$=/$C_6$) | Conversion ($C_2$=) | Catalyst Productivity (g $1-C_6$=/g Cr) |
|---|---|---|---|---|
| 19 | 92.0% | 98.9% | 74.4% | 80,252 |
| 20 | 92.5% | 99.1% | 71.8% | 77,877 |

The addition of TEA provided a catalyst with increased activity. It can also reduce corrosion in downstream equipment after the catalyst is inactivated.

Example 9

Several catalysts, catalysts 21-23 were prepared in which the molar ratio of the 2,5-dimethylpyrrole/chromium was varied during the addition to the solution of aluminum alkyls.

Catalyst 21: A chromium solution of 4.61 g chromium (III) 2-ethylhexanoate dissolved in 2.27 g ethylbenzene was divided into four equal portions of 1.72 g each. To each of these portions was added a different amount of 2,5-dimethylpyrrole. To the first was added 1.52 g 2,5-dimethylpyrrole, to the second 0.84 g, to the third 0.27 g and to the fourth 0.12 g. The chromium/2,5-dimethylpyrrole portions were then added sequentially to a solution containing 12.07 g neat triethylaluminum (TEA), 9.29 g neat diethylaluminum chloride (DEAC) and 20.01 g ethylbenzene. The total addition time was approximately 50 minutes. The resulting catalyst solution was diluted to 100 mL with ethylbenzene. The results from testing of this catalyst, in a 1 L continuous reactor, are shown as Catalyst 21 in Table 9 below. The results shown are the average of four separate test runs.

Catalyst 22: A chromium solution of 4.61 g chromium (III) 2-ethylhexanoate dissolved in 2.27 g ethylbenzene was divided into four portions. To each of these portions was added a different amount of 2,5-dimethylpyrrole and a similar amount of ethylbenzene. The first portion contained 0.69 g chromium solution, 1.50 g 2,5-dimethylpyrrole and 7.51 g ethylbenzene. The second contained 1.38 g chromium solution, 0.81 g 2,5-dimethylpyrrole and 7.52 g ethylbenzene. The third portion contained 2.06 g chromium solution, 0.27 g 2,5-dimethylpyrrole and 7.50 g ethylbenzene. The fourth portion contained 2.75 g chromium solution, 0.16 g 2,5-dimethylpyrrole and 7.51 g ethylbenzene. The chromium/2,5-dimethylpyrrole/ethylbenzene portions were then added sequentially to a solution containing 12.07 g neat triethylaluminum (TEA), 9.27 g neat diethylaluminum chloride (DEAC) and 25.01 g ethylbenzene. The total addition time was approximately 60 minutes. The resulting catalyst solution was then diluted to 100 mL with ethylbenzene. The results from testing of this catalyst, in a 1 L continuous reactor, are shown as Catalyst 22 in Table 9 below. The results shown are the average of two separate test runs.

Catalyst 23: A chromium solution of 4.61 g chromium (III) 2-ethylhexanoate dissolved in 2.27 g ethylbenzene was divided into four portions. To each of these portions was added a different amount of 2,5-dimethylpyrrole and a similar amount of ethylbenzene. The first portion contained 0.35 g chromium solution, 1.53 g 2,5-dimethylpyrrole and 7.51 g ethylbenzene. The second contained 0.69 g chromium solution, 0.81 g 2,5-dimethylpyrrole and 7.49 g ethylbenzene. The third portion contained 2.06 g chromium solution, 0.27 g 2,5-dimethylpyrrole and 7.51 g ethylbenzene. The fourth portion contained 3.77 g chromium solution, 0.15 g 2,5-dimethylpyrrole and 7.50 g ethylbenzene. The chromium/2,5-dimethylpyrrole/ethylbenzene portions were then added sequentially to a solution containing 12.09 g neat triethylaluminum (TEA), 9.26 g neat diethylaluminum chloride (DEAC) and 25.02 g ethylbenzene. The total addition time was approximately 60 minutes. The resulting catalyst solution was then diluted to 100 mL with ethylbenzene. The results from testing of this catalyst, in a 1 L continuous reactor, are shown as Catalyst 23 in Table 9 below. The results shown are the average of two separate test runs.

Example 10

Catalyst 24: To a dry, nitrogen purged 5 gallon reactor was added 14.6 lbs of dry, nitrogen purged ethylbenzene. The reactor was purged with nitrogen and a mixture consisting of 1,592 g neat triethylaluminum (TEA) and 1,238 g neat diethylaluminum chloride (DEAC) was added to the reactor. The aluminum alkyl mix vessel was rinsed with 0.2 lbs of ethylbenzene and this rinse was added to the reactor. A chromium solution was prepared by adding 700 mL of ethylbenzene to 630.9 g chromium (III) 2-ethylhexanoate. The mixture was stirred until solution was obtained and was transferred to a 1 gallon cylinder followed by a 75 mL ethylbenzene rinse. The cylinder, containing the chromium solution, was pressured and depressured several times with nitrogen. Chromium/2,5-dimethylpyrrole (DMP) mixtures were added to the reactor in four batches from a chromium/DMP mix tank. For the first batch 65 g of chromium and 233 mL DMP were added to the mix tank and then this mixture was added to the reactor in 31-52 g increments with stirring and cooling so the temperature did not exceed 22° C. For the second batch 130 g of chromium and 97 mL DMP were added to the mix tank and then this mixture was added to the reactor in 48-58 g increments with stirring and cooling so the temperature did not exceed 22° C. For the third batch 326 g of chromium and 39 mL DMP were added to the mix tank and then this mixture was added to the reactor in 48-54 g increments with stirring and cooling so the temperature did not exceed 22° C. For the fourth batch 789 g of chromium and 20 mL DMP were added to the mix tank and then this mixture was added to the reactor in 100-130 g increments with stirring and cooling so the temperature did not exceed 24° C. Ethylbenzene (1 lb) was added to the chromium solution cylinder and used to rinse the chromium/DMP mix tank. The ethylbenzene rinse was then added to the reactor. The reactor was stirred for an additional 30 minutes. After standing overnight the catalyst solution was filtered, using a filter as described above. The catalyst solution was tested for activity in a 1 L continuous reactor. The results are shown as Catalyst 24 in Table 9 below. The results shown are the average of two separate test runs.

Example 11

Catalyst 25: To a dry, nitrogen purged 5 gallon reactor was added 14.0 lbs of dry, nitrogen purged ethylbenzene. The reactor was purged with nitrogen and a mixture consisting of 1,283 g neat triethylaluminum (TEA) and 990 g neat diethylaluminum chloride (DEAC) was added to the reactor. The aluminum alkyl mix vessel was rinsed with 0.2 lbs of ethylbenzene and this rinse was added to the reactor. A chromium solution was prepared by adding 700 mL of ethylbenzene to 630.9 g chromium (III) 2-ethylhexanoate. The mixture was stirred until solution was obtained and was transferred to a 1 gallon cylinder followed by a 75 mL ethylbenzene rinse. The cylinder, containing the chromium solution, was pressured and depressured several times with nitrogen. Chromium/2,5-dimethylpyrrole (DMP) mixtures were added to the reactor in four batches from a chromium/DMP mix tank. For the first batch 52 g of chromium and 187 mL DMP were added to the mix tank and then this mixture was added to the reactor in 20-52 g increments with stirring and cooling so the temperature did not exceed 21° C. For the second batch 104 g of chromium and 78 mL DMP were added to the mix tank and then this mixture was added to the reactor in 40-50 g increments with stirring and cooling so the temperature did not exceed 22° C. For the third batch 261 g of chromium and 31 mL DMP were added to the mix tank and then this mixture was added to the reactor in 90-101 g increments with stirring and cooling so the temperature did not exceed 23° C. For the fourth batch 625 g of chromium and 16 mL DMP were added to the mix tank and then this mixture was added to the reactor in 30-108 g increments with stirring and cooling so the temperature did not exceed 23° C.

To the TEA/DEAC mix vessel was added 327 g neat TEA and 256 g neat DEAC. To the chromium/DMP mix tank was added 261 g of the chromium solution. To a separate cylinder connected to the reactor was added 78 mL of DMP. The reactor pressure was increased with nitrogen and the valves connecting each of the above cylinders to the reactor were opened. Reducing the reactor pressure transferred the contents of each of these vessels simultaneously to the reactor while the reactor was being stirred and cooled. An increase of 1° C. (20° C. to 21° C.) was observed in the reactor temperature upon addition of the catalyst components.

Ethylbenzene (0.4 lb) was added to the chromium solution cylinder and used to rinse the chromium/DMP mix tank. The ethylbenzene rinse was then added to the reactor. Ethylbenzene (0.5 lb) was added to the DMP cylinder. This rinse of the DMP cylinder was added to the reactor. Ethylbenzene (0.2 lb) was added to the aluminum alkyl mix vessel and then pressured into the reactor. The reactor was stirred for an additional 30 minutes. After standing overnight the catalyst solution was filtered, using a filter as described above. The catalyst solution was tested for activity in a 1 L continuous reactor. The results are shown as Catalyst 25 in Table 9. The results shown are the average of three separate test runs.

TABLE 9

| Catalyst | Selectivity ($1\text{-}C_6=$) | Purity ($1\text{-}C_6=/C_6$) | Conversion ($C_2=$) | Catalyst Productivity (g $1\text{-}C_6=$/g Cr) |
| --- | --- | --- | --- | --- |
| 21 | 92.6% | 98.8% | 75.1% | 81,432 |
| 22 | 91.2% | 99.1% | 77.6% | 82,927 |
| 23 | 90.5% | 99.1% | 79.7% | 84,536 |
| 24 | 91.0% | 99.2% | 87.5% | 93,397 |
| 25 | 90.9% | 99.0% | 86.6% | 92,297 |

Catalysts 21-24 show that varying the chromium to pyrrole ratio in a decreasing manner produces a catalyst which has increased selectivity, product purity, and productivity. Catalyst 25 demonstrates the separate simultaneous addition of catalyst components to a heel of active catalyst.

Example 12

Two catalysts were prepared, catalyst 26 and catalyst 27, with the addition of a nitrogen compound to the alkylaluminum compound to solubilize products resulting from the reaction of water and aluminum alkyls.

Catalyst 26: To a dry 100 mL volumetric flask was added 25.01 g ethylbenzene, 12.07 g neat triethylaluminum (TEA) and 9.27 g neat diethylaluminum chloride (DEAC) and 0.34 g tributylamine. To this was added a solution containing 4.61 g chromium (III) 2-ethylhexanoate, 2.27 g ethylbenzene and 2.74 g 2,5-dimethylpyrrole. Ethylbenzene was then added to provide a total volume of 100 mL. Upon standing overnight no film was observed in the neck of the flask and no precipitate was observed. When the amine was not added to the catalyst preparation a film was observed upon standing overnight. A film was observed in the neck of the flask after standing for an additional 24 hours. This catalyst was tested for activity in a 1 L continuous reactor. The results of two separate test runs are shown in Table 10 below as Catalyst 26.

Catalyst 27: To a dry 100 mL volumetric flask was added 25.01 g ethylbenzene, 12.07 g neat triethylaluminum (TEA) and 9.27 g neat diethylaluminum chloride (DEAC) and 0.34 g tributylamine. To this was added a solution containing 4.61 g chromium (III) 2-ethylhexanoate, 2.27 g ethylbenzene, 2.74 g 2,5-dimethylpyrrole and 1.06 g tributylamine. Ethylbenzene was then added to provide a total volume of 100 mL. Upon standing overnight no film was observed in the neck of the flask and no precipitate was observed. When the amine was not added to the catalyst preparation a film was observed upon standing overnight. A film was observed in the neck of the flask after standing for an additional 24 hours. This catalyst was tested for activity in a 1 L continuous reactor. The results of two separate test runs are shown in Table 10 as Catalyst 27.

TABLE 10

| Catalyst | Selectivity ($1\text{-}C_6=$) | Purity ($1\text{-}C_6=/C_6$) | Conversion ($C_2=$) | Catalyst Productivity (g $1\text{-}C_6=$/g Cr) |
| --- | --- | --- | --- | --- |
| 26 | 93.0% | 99.2% | 70.4% | 76,697 |
| 27 | 92.8% | 99.2% | 69.5% | 75,574 |

The example shows that the addition of an amine to the alkylaluminum compounds inhibits formation of detrimental precipitation from the catalyst solution.

Example 13

Catalyst 28: Chromium (III) 2-ethylhexanoate (18.44 g) dissolved in 9.1 g ethylbenzene produces a viscous solution. When 2,5-dimethylpyrrole (10.96 g) was added to this viscous solution a much thinner solution results. This thinner solution is much more adaptable to water removal by molecular sieves. Activated 3 A molecular sieves (15.05 g) were added to the chromium/pyrrole/ethylbenzene solution and allowed to stand with periodic shaking for 22 days before catalyst preparation. A solution was prepared in a 100 mL volumetric flask consisting of ethylbenzene (25.00 g), neat triethylaluminum (12.07 g) and neat diethylaluminum chloride (9.26 g). To this aluminum alkyl solution was added 9.62 g of the dried chromium/pyrrole/ethylbenzene solution and the resulting catalyst was diluted to 100 mL with additional ethylbenzene. After standing overnight a film was observed in the neck of the flask but no precipitate was observed in the flask. This catalyst was tested in a 1 L continuous reactor and an average of two separate test runs is shown in Table 11 as Catalyst 28. A control using undried chromium/pyrrole/ethylbenzene solution was made at the same time. After standing overnight a film was observed in the neck of the flask and a precipitate was also observed. This catalyst was tested in a 1 L continuous reactor and an average of two separate test runs is shown in Table 11 as Catalyst 29.

TABLE 11

| Catalyst | Selectivity ($1\text{-}C_6=$) | Purity ($1\text{-}C_6=/C_6$) | Conversion ($C_2=$) | Catalyst Productivity (g $1\text{-}C_6=$/g Cr) |
| --- | --- | --- | --- | --- |
| 28 | 93.2% | 99.4% | 76.0% | 83,056 |
| 29 | 94.3% | 99.3% | 64.5% | 71,312 |

In addition to the improved catalyst productivity as shown, reduced downstream corrosion could be obtained using the dried catalyst components.

Example 14

Catalyst 30-31: Chromium (III) 2-ethylhexanoate (222.10 g) was added to a round bottom flask equipped with a Dean- Stark tube. Ethylbenzene (147.39 g) was added and the flask was heated to reflux the contents. Reflux was continued until water no longer accumulated in the Dean-Stark tube. Ethylbenzene and water (27.13 g) were discarded from the Dean-Stark tube. This chromium solution was used to make catalyst by adding it to a 100 mL volumetric flask containing ethylbenzene (16.73 g), neat triethylaluminum (12.28 g), neat diethylaluminum chloride (9.26 g) and 2,5-dimethylpyrrole (2.74 g). Ethylbenzene was subsequently added to dilute the catalyst to a 100 mL volume. This catalyst was tested in a 1 L continuous reactor. The results of the test (two catalyst preparations and three separate test runs) are shown in Table 12 as Catalyst 30. A control catalyst prepared similarly but with chromium (III) 2-ethylhexanoate that had not been azeotrope dried was used. The results of testing the undried preparation are shown as Catalyst 31 in Table 12.

TABLE 12

| Catalyst | Selectivity $(1-C_6\!\!=\!\!)$ | Purity $(1-C_6\!\!=\!\!/C_6)$ | Conversion $(C_2\!\!=\!\!)$ | Catalyst Productivity $(g\ 1-C_6\!\!=\!\!/g\ Cr)$ |
|---|---|---|---|---|
| 30 | 89.4% | 98.7% | 81.5% | 84,462 |
| 31 | 88.5% | 98.8% | 82.3% | 85,400 |

The example shows that drying the chromium component by azeotropic distillation prepares an effective catalyst and also will reduce equipment corrosion.

Example 15

Figure 5:
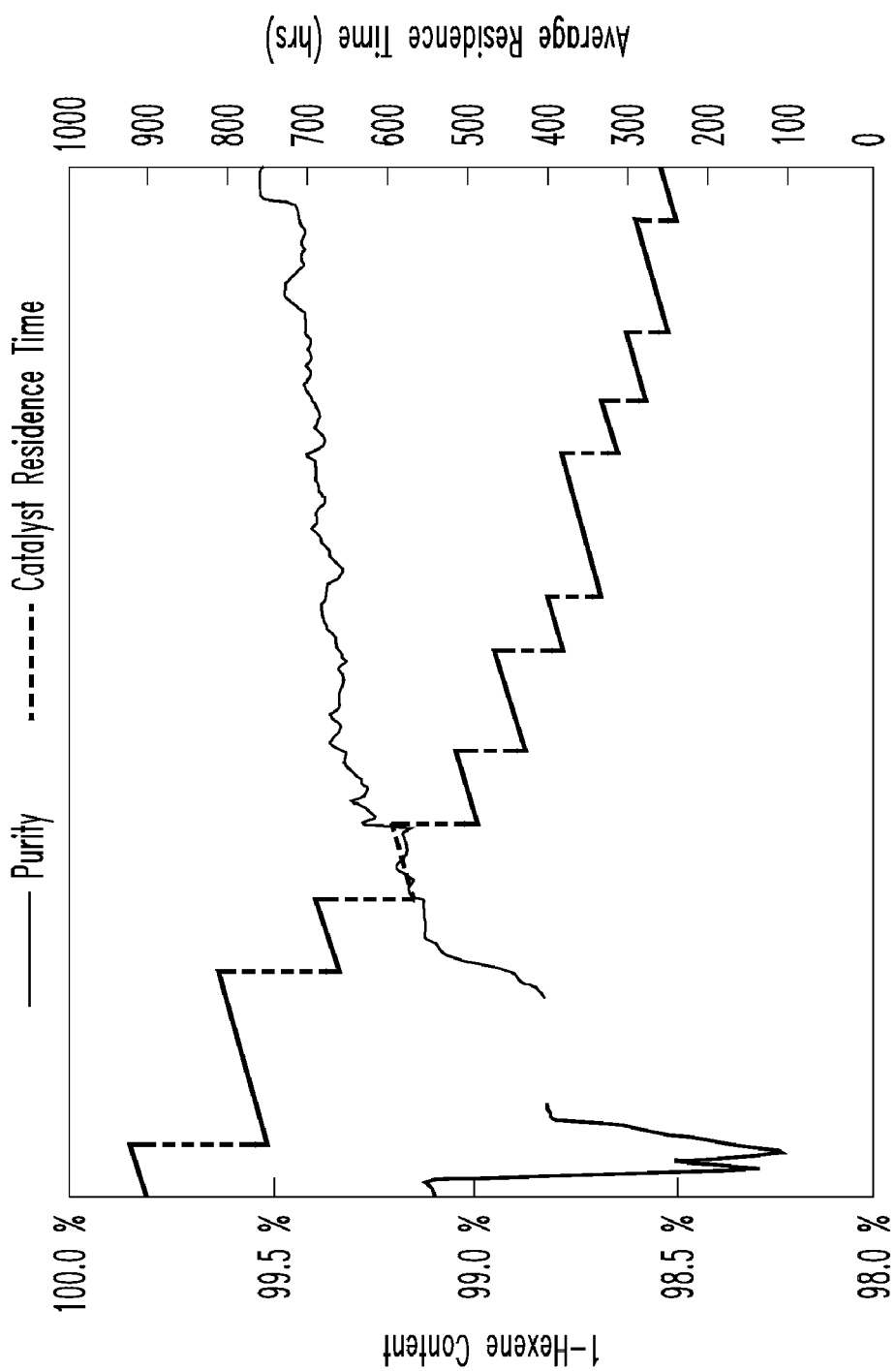
FIG. 5 is a graph of the average catalyst residence time (i.e. catalyst age) versus the purity of hexene produced.

An ethylene trimerization catalyst composition was prepared using methods known to those skilled in the art, placed in the catalyst feed tank (under inert conditions) of a continuous 1-hexene production process, and aged for approximately 900 hours. The continuous 1-hexene production process was then started using the aged catalyst in the feed tank for the trimerization of ethylene to 1-hexene. Periodically, additional fresh ethylene trimerization catalyst was prepared and added to the catalyst used in the continuous 1-hexene production process. The average age of the ethylene oligomerization catalyst composition periodically calculated to determine the average time the catalyst had resided in the catalyst feed tank based upon the average catalyst composition in the catalyst feed tank. Throughout the continuous 1-hexene production process, samples of the continuous 1-hexene production process product we removed and analyzed for 1-hexene content. FIG. 5 shows the impact of the average catalyst residence time (i.e. catalyst age) on the purity of the hexene production produced by the continuous 1-hexene production process. FIG. 5 indicates that the purity of the 1-hexene product is negatively impacted by increasing age of the ethylene trimerization catalyst.

What is claimed is:

1. A method of oligomerizing olefins, comprising:
    (A) preparing an oligomerization catalyst, wherein:
        (i) the catalyst comprises a chromium-containing compound, a pyrrole-containing compound, a non-halide metal alkyl, a metal halide-containing compound, and optionally a solvent, and
        (ii) the catalyst is prepared by:
            (a) contacting a composition comprising the chromium-containing compound with a portion of the non-halide metal alkyl such that the molar ratio of non-halide metal alkyl to chromium-containing compound is less than about 1.5:1, and
            (b) subsequently contacting the components from (a) with a composition comprising the metal halide-containing compound and the remaining components of the catalyst compound including an additional amount of the non-halide metal alkyl; and
    (B) oligomerizing olefins by contact with the catalyst in a reaction zone.

2. The method of claim 1 wherein productivity of the catalyst in step (B) is greater than productivity of an otherwise similar catalyst prepared by: contacting a composition comprising the chromium-containing compound with a portion of a composition comprising the metal halide-containing compound prior to or simultaneous with contact of the composition comprising the chromium-containing compound with a portion of the non-halide metal alkyl.

3. The method of claim 2 wherein the metal halide containing compound is an alkylaluminum halide compound and the non-halide metal alkyl is a trialkylaluminum compound.

4. The method of claim 1 further comprising: (C) contacting an effluent from the reaction zone with an alcohol to kill the catalyst.

5. The method of claim 4 wherein corrosion is reduced in equipment after the catalyst has been deactivated in comparison to deactivation of a catalyst prepared by: contacting a composition comprising the chromium-containing compound with all or a portion of a composition comprising the metal halide-containing compound prior to or simultaneous with contact of the composition comprising the chromium-containing compound with a portion of the non-halide metal alkyl.

6. The method of claim 5 wherein the metal halide containing compound is an alkylaluminum halide and the non-halide metal alkyl is a trialkylaluminum compound.

7. The method of claim 1, wherein the composition comprising the chromium-containing compound further comprises water, acidic protons, or both.

8. The method of claim 7, wherein the portion of the non-halide metal alkyl in step (ii)(a) is an amount effective to abate substantially all available water, acidic protons, or both from the composition comprising the chromium-containing compound.

9. The method of claim 8, wherein the acidic protons are provided by 2-ethylhexanoic acid.

10. The method of claim 8, wherein water, acidic protons, or both are abated by the addition of a non-halide metal alkyl to the composition comprising the chromium-containing compound in an amount that is about a 200 percent excess of an amount sufficient to abate at least about 100 percent of the water, acidic protons, or both.

11. The method of claim 8, wherein the abatement of water reduces the formation of precipitate in comparison to an otherwise similar catalyst prepared by: contacting a composition comprising the chromium-containing compound with all or a portion of a composition comprising the metal halide-containing compound prior to or simultaneous with contact of the composition comprising the chromium-containing compound with a portion of the non-halide metal alkyl.

12. The method of claim 11, wherein the reduction in precipitates improves selectivity in step (B).

13. The method of claim 1, wherein the non-halide metal alkyl comprises an alkylaluminum compound.

14. The method of claim 1, wherein the composition comprising the metal halide-containing compound comprises an alkylaluminum halide.

15. The method of claim 1 wherein the composition comprising the chromium-containing compound comprises a chromium carboxylate.

16. The method of claim 1, wherein the non-halide metal alkyl comprises an alkylaluminum compound, the composition comprising the metal halide-containing compound in step (ii)(b) comprises an alkylaluminum halide and a trialkylaluminum compound, and the composition comprising the chromium-containing compound in step (ii)(a) comprises a chromium carboxylate.

17. The method of claim 1, wherein the non-halide metal alkyl comprises triethylaluminum compound, the composition comprising the metal halide-containing compound in step (ii)(b) comprises a diethyl aluminum chloride and triethylaluminum, and the composition comprising the chromium-containing compound in step (ii)(a) comprises chromium (III) 2-ethylhexanoate.

18. The method of claim 3 wherein the alkylaluminum halide compound is DEAC and the trialkylaluminum compound is TEA.

19. The method of claim 6 wherein the alkylaluminum halide compound is DEAC and the trialkylaluminum compound is TEA.

* * * * *